(12) United States Patent
Peters et al.

(10) Patent No.: US 7,323,310 B2
(45) Date of Patent: Jan. 29, 2008

(54) METHODS AND COMPOSITIONS FOR RNA AMPLIFICATION AND DETECTION USING AN RNA-DEPENDENT RNA-POLYMERASE

(75) Inventors: Lars-Erik Peters, Lafayette, CO (US); Michael Domanico, Middleton, WI (US); Sven Buelow, Hamburg (DE)

(73) Assignee: Qiagen North American Holdings, Inc., Valencia, CA (US)

( * ) Notice: Subject to any disclaimer, the term of this patent is extended or adjusted under 35 U.S.C. 154(b) by 0 days.

(21) Appl. No.: 11/217,972

(22) Filed: Aug. 31, 2005

(65) Prior Publication Data

US 2006/0073500 A1   Apr. 6, 2006

Related U.S. Application Data

(60) Provisional application No. 60/606,222, filed on Aug. 31, 2004.

(51) Int. Cl.
*C12Q 1/68* (2006.01)
*C12P 19/34* (2006.01)
*C07H 21/04* (2006.01)
*C07K 13/00* (2006.01)

(52) U.S. Cl. .................. 435/6; 435/91.2; 435/91.51; 435/174; 536/22.1; 530/350

(58) Field of Classification Search ............ 435/6, 435/91.2, 91.51; 536/22.1; 530/350
See application file for complete search history.

(56) References Cited

U.S. PATENT DOCUMENTS

| | | | |
|---|---|---|---|
| 4,458,006 A | 7/1984 | Donges et al. | |
| 6,218,142 B1 | 4/2001 | Wassenegger et al. | |
| 6,294,658 B1 | 9/2001 | Famodu et al. | |
| 6,506,559 B1 | 1/2003 | Fire et al. | |
| 6,677,146 B1 * | 1/2004 | Janjic et al. | 435/194 |
| 2002/0086365 A | 7/2000 | Tuschl et al. | |
| 2001/0023067 A1 | 9/2001 | Wassenegger et al. | |
| 2003/0124559 A1 | 7/2003 | Makeyev et al. | |
| 2005/0059019 A1 | 3/2005 | Bulow et al. | |

FOREIGN PATENT DOCUMENTS

| WO | WO 01/46396 A1 | 6/2001 |
|---|---|---|
| WO | WO 02/44321 A2 | 6/2002 |

OTHER PUBLICATIONS

Sequence searched report Accession No. AR145904, 1998.*
Makeyev, E., et al., "Primer-independent RNA sequencing with bacteriophage φ6 RNA polymerase and chain terminators," *RNA* 7:774-781 (2001).
Schiebel, W., et al., "RNA-directed RNA polymerase from tomato leaves. I. Purification and physical properties," *J. Biol. Chem.* 268(16):11851-11857 (Jun. 1993).
Neufeld et al., 1991, Purification, Characterization, and Comparison of Poliovirus RNA Polymerase from Native and Recombinant Sources, J.Biol.Chem., 1991, 266(35), pp. 24212-24219.
Van Gelder et al., Amplified RNA Synthesized from Limited Quantities of Hetrogenous cDNA, Proc. Natl. Acad. Sci, 1990,87(5), pp. 1663-1666.
Tijsterman et al, Dicers at RISC: the mechanism of RNAi, Cell, Apr. 2, 2004; 117(1), pp. 1-3.
Lipardi et. al, RNAi as Random Degradative PCR: siRNA Primers Convert mRNA into dsRNAs that Are Degraded to Generate New siRNAs, Cell , 2001, 107(3), pp. 297-307.
Sijen et al., On the Role of RNA Amplification in dsRNA-Triggered Gene Silencing, Cell, 2001, 107(4), pp. 465-475.
Hannon, G. J., RNA Interference, Nature, Jul. 11, 2002, 418 (6894), pp. 244-251.
Summers and Smith, 1987, Texas Agriculture Experiment Station Bulletin, 1555.
Puck et al., Genetics of somatic mammalian cells, VII. Induction and isolation of nutritional mutants in Chinese hamster cells., Proc Natl Acad Sci , May 27, 1968; 60, pp. 1275-1281.
Sambrook, Fritsch & Maniatis, Molecular Cloning: A Laboratory Manual, Second Edition (1989).
Perbal, A Practical Guide to Molecular Cloning (1984).
Hames & Higgins, eds., Nucleic Acid Hybridization (1984).
Schiebel et al., Isolation of an RNA-directed RNA polymerase-specific cDNA clone from tomato, Plant Cell, Dec. 2003; (10), pp. 2087-101.
Ahlquist, RNA-dependent RNA polymerases, viruses, and RNA silencing, Science, May 17, 2002; 296(5571), pp. 1270-1273. Review.
Cogoni et al., Gene silencing in *Neurospora crassa* requires a protein homologous to RNA-dependent RNA polymerase, Nature, May 13, 1999, 399(6732), pp. 166-169.
Iyer et al., Evolutionary connection between the catalytic subunits of DNA-dependent RNA polymerases and eukaryotic RNA-dependent RNA polymerases and the origin of RNA polymerases, BMC Structural Biology, Jan. 28, 2003; 3(1), p. 1.
Hammond, Argonaute2, a link between genetic and biochemical analyses of RNAi, Science, Aug. 10, 2001; 293(5532), pp. 1146-1150.
Luo et al., De novo initiation of RNA synthesis by the RNA-dependent RNA polymerase (NS5B) of hepatitis C virus, J. Virol., Jan. 2000, 74(2):851-863.
Schiebel et al., RNA-directed RNA polymerase from tomato leaves. II. Catalytic in vitro properties, J. Biol. Chem., Jun. 5, 1993; 268(16), pp. 11858-110867.

(Continued)

*Primary Examiner*—Kenneth R. Horlick
*Assistant Examiner*—Joyce Tung
(74) *Attorney, Agent, or Firm*—Dorsey & Whitney LLP

(57) ABSTRACT

Methods and compositions are provided for amplifying RNA from an RNA template. Methods and compositions are further provided for detecting an RNA in an RNA containing sample. Compositions used for the amplification of RNA from RNA include a RNA-dependent RNA-polymerase, a RNA helicase, and an energy source. Illustrative RNA-dependent RNA-polymerase enzymes are derived from the tomato or tobacco plant, while illustrative RNA helicase enzymes include the eIF4A and eIF4B proteins.

16 Claims, 4 Drawing Sheets

OTHER PUBLICATIONS

Tang et al., A biochemical framework for RNA silencing in plants, Genes and Dev., Jan. 1, 2003; 17(1), pp. 49-63.

Ikegami et al., RNA-dependent RNA polymerase of tobacco plants, Proc. Natl. Acad. Sci, May 1978, 75(5), pp. 2122-2124.

Khan et al., RNA-directed RNA polymerases from healthy and from virus-infected cucumber, Proc. Natl. Acad. Sci., Apr. 1986, 83(8), pp. 2383-2386.

Ranjith-Kumar et al., Terminal nucleotidyl transferase activity of recombinant Flaviviridae RNA-dependent RNA polymerases: implication for viral RNA synthesis, J. Virology, Sep. 2001; 75(18), pp. 8615-8623.

Pfeiffer et al., A single mutation in poliovirus RNA-dependent RNA polymerase confers resistance to mutagenic nucleotide analogs via increased fidelity, Proc Natl Acad Sci, Jun. 10, 2003, 100(12), pp. 7289-7294.

Western et al., HUA Enhancer2, a putative DExH-box RNA helicase, maintains homeotic B and C gene expression in *Arabidopsis*, Development, Apr. 12, 2002; 9(7), pp. 1569-1581.

Pause et al., Mutational analysis of a DEAD box RNA helicase: the mammalian translation initiation factor eIF-4A, EMBO J., Jul. 11, 1992; 11(7), pp. 2643-2654.

Chamot et al., A cold shock-induced cyanobacterial RNA helicase, J Bacteriol., Mar. 1999; 181(6), pp. 1728-1732.

Jones, et al., Cold shock induces a major ribosomal-associated protein that unwinds double-stranded RNA in *Escherichia coli*, Proc Natl Acad Sci., Jan. 9, 1996; 93(1), pp. 76-80.

Jiang et al., The role of the 5'-end untranslated region of the mRNA for CspA, the major cold-shock protein of *Escherichia coli*, in cold-shock adaptation, J. Bacteriol., Aug. 1996; 178(16), pp. 4919-4925.

Ortlepp et al., The mammalian homologue of Prp16p is overexpressed in a cell line tolerant to Leflunomide, a new immunoregulatory drug effective against rheumatoid arthritis, RNA, Aug. 1998; 4(8), pp. 1007-1018.

Lee et al., A new RNA helicase isolated from HeLa cells that catalytically translocates in the 3' to 5' direction, J Biol Chem., Mar. 5, 1992; 267(7), pp. 4398-4407.

Rogers et al., Further characterization of the helicase activity of eIF4A. Substrate specificity, J Biol Chem., Apr. 20, 2001; 276(16), pp. 12598-12608.

Maniatis et al., Molecular Cloning: A Laboratory Manual, New York: Cold Spring Harbor Laboratory, 1982, pp. 280-281.

Beaucage et al., Deoxynucleoside phosphoramidites—A new class of key intermediates for deoxypolynucleotide synthesis, Tetrahedron Letters, 1981, 22(20), pp. 1859-1862.

Yang, D., RNA interference (RNAi) with RNase III-prepared siRNAs, Methods Mol Biol., 2004, 252, pp. 471-482.

Zamore et al, RNAi: double-stranded RNA directs the ATP-dependent cleavage of mRNA at 21 to 23 nucleotide intervals, Cell, Mar. 31, 2000; 101(1), pp. 25-33.

Pause, et al., The HRIGRXXR region of the DEAD box RNA helicase eukaryotic translation initiation factor 4A is required for RNA binding and ATP hydrolysis, Mol Cell Biol., Nov. 1993; 13(11), pp. 6789-6798.

Domingo, et al., Basic concepts in RNA virus evolution, The FASEB Journal, Jun. 1996, vol. 10, pp. 859-864.

Pugachev, et al., High Fidelity of Yellow Fever Virus RNA Polymerase, J. Virol., Jan. 2004, 78(2), pp. 1032-1038.

\* cited by examiner

SEQUENCE LISTING

```
<160> NUMBER OF SEQ ID NOS: 6

<210> SEQ ID NO 1
<211> LENGTH: 3395
<212> TYPE: DNA
<213> ORGANISM: Tomato

<400> SEQUENCE: 1
gaattcccat gggtaaaact attcaagtgt tcggctttcc atacctgctg tctgctgaag     60
ttgtcaagag cttcctggag aaatacaccg gttacgtac ggtttgtgct ctggaagtta    120
agcaatccaa aggtggctcc cgtgctttcg caaaagtaca gttcgctgac aacatctctg    180
cggacaaaat cattaccctg gctaacaacc gtctgtattt cggttcctcc tatctgaaag    240
cgtgggaaat gaaaaccgac atcgttcagc tgcgtgctta cgtagatcag atggacggca    300
```

-continued

| | |
|---|---|
| tcaccctgaa ctttggctgt cagatcagcg acgacaaatt cgcggtactg ggttccaccg | 360 |
| aagtatctat ccagttcggc atcggcctga aaaagttctt tttcttcctg tcctctggta | 420 |
| gcgccgatta caaactgcag ctgtcttatg aaaacatctg gcaggttgtc ctgcaccgcc | 480 |
| cgtatggtca gaacgctcag tttctgctga ttcagctgtt cggtgctcct cgtatttaca | 540 |
| aacgtctgga aaactcctgc tactccttct caaagaaac cccggacgac cagtgggttc | 600 |
| gtaccaccga tttcccaccg tcttggattg gcctgagctc tagcctgtgc ctgcagttcc | 660 |
| gtcgcggcgt ccgcctgccg aactttgaag aatccttctt tcactacgcg aacgtgaga | 720 |
| acaacattac cctgcagacc ggcttcactt tcttcgtttc tcagaaatct gcgctggtcc | 780 |
| cgaacgttca gccgccggag ggtatctcta cccgtataa aatcctgttc aaaatctcct | 840 |
| ccctggtgca gcacggttgc attccgggtc cggcgctgaa cgtttacttt tccgtctgg | 900 |
| ttgacccgcg tcgtcgtaat gtcgcctgta ttgagcacgc tctggaaaag ctgtactaca | 960 |
| tcaaagaatg ctgctacgac ccggttcgtt ggctgaccga gcagtacgat ggctacctga | 1020 |
| aaggtcgtca gccgccgaaa agcccaagca tcactctgga tgatggcctg gtgtacgttc | 1080 |
| gccgcgttct ggttactcct tgcaaagttt atttctgtgg tccggaagtg aacgttagca | 1140 |
| accgtgtact gcgcaactat tctgaagata tcgataattt tctgcgtgta tctttcgttg | 1200 |
| atgaagaatg ggaaaaactg tactctactg acctgctgcc gaaggcttct actggttccg | 1260 |
| gtgttcgcac gaacatctac gaacgtatcc tgtctaccct gcgcaaaggt ttcgttattg | 1320 |
| gcgacaaaaa gttcgagttc ctggcgttct cttcttccca gctgcgcgac aacagcgttt | 1380 |
| ggatgtttgc ctctcgtccg ggtctgactg cgaacgacat ccgcgcctgg atgggcgact | 1440 |
| tcagccagat caagaatgtt gcaaaatacg cggctcgtct gggtcagtcc tttggctcca | 1500 |
| gccgtgaaac tctgtctgta ctgcgtcacg aaatcgaagt tattcctgac gtcaaagtgc | 1560 |
| acggtactag ctacgtattc tctgatggta tcggcaaaat ctccggtgac ttcgcccacc | 1620 |
| gcgttgcctc caaatgtggt ctgcagtaca ctccgtctgc gttccagatt cgttacggtg | 1680 |
| gctacaaagg cgtggtaggc gtagatccgg actcttctat gaagctgtcc ctgcgtaaat | 1740 |
| ccatgtctaa gtatgaatcc gataacatca aactggatgt tctgggctgg tccaagtacc | 1800 |
| agccgtgcta cctgaaccgc cagctgatca ccctgctgtc cactctgggt gttaaagacg | 1860 |
| aggttctgga gcagaagcag aaagaagcag ttgatcagct ggacgctatc ctgcacgaca | 1920 |
| gcctgaaggc acaggaagct ctggaactga tgtccccggg tgaaaatact aatattctga | 1980 |
| aggccatgct gaactgcggc tacaaaccgg acgctgaacc tttcctgtcc atgatgctgc | 2040 |
| agaccttccg tgcgtccaaa ctgctggacc tgcgtacccg tagccgtatt ttcatcccga | 2100 |
| acggtcgcac tatgatgggt tgtctggatg aatcccgtac cctggaatac ggtcaggtgt | 2160 |
| ttgtgcaatt caccggcgca ggtcatggcg agttttctga tgacctgcac ccgtttaata | 2220 |
| acagccgttc tactaactcc aacttcatcc tgaagggtaa cgttgtggtt gcaaagaacc | 2280 |
| cgtgcctgca cccgggtgac atccgtgtgc tgaaagccgt aaatgtacgt gcactgcacc | 2340 |
| atatggtaga ttgcgtggta ttcccgcaga aaggcaagcg tccgcatcca aatgaatgct | 2400 |
| ctggctccga tctggacggt gatatctatt cgtttgctg ggaccaggac atgatcccgc | 2460 |
| cacgtcaggt tcagccgatg gaatacccgc ggctccatc tatccagctg gaccacgatg | 2520 |
| ttactatcga ggaagttgaa gaatatttca ccaactatat tgtgaacgac tctctgggca | 2580 |
| tcatcgcgaa cgcccatgtc gtgttcgcgg accgtgagcc ggacatggct atgtctgacc | 2640 |

-continued

```
cgtgcaagaa actggcggaa ctgttttcta tcgcagttga ctttccgaaa accggcgtgc    2700
ctgcggaaat cccaagccag ctgcgtccga aagaataccc ggacttcatg gataaaccgg    2760
ataaaacctc ttacatttct gaacgtgtta tcggcaaact gttccgtaaa gtcaaggaca    2820
aagcacctca agcgagcagc attgcaactt tcactcgcga cgtagctcgt cgttcttatg    2880
acgccgatat ggaagttgac ggtttcgaag attatatcga tgaggcattt gactataaaa    2940
cggaatatga caacaaactg gcaatctga tggactacta cggtatcaaa acggaagccg     3000
aaatcctgag cggtggtatc atgaaagcct ctaagacgtt cgatcgtcgt aaggacgctg    3060
aagcgatttc tgtggcggtt cgtgcgctgc gcaaagaggc tcgtgcgtgg ttcaaacgcc    3120
gtaacgatat tgacgatatg ctgccgaaag cctccgcttg gtatcacgtt acgtatcacc    3180
ctacgtactg gggctgctat aaccaaggtc tgaagcgcgc tcacttcatt agcttcccgt    3240
ggtgcgttta cgaccagctg atccagatta agaaagataa agctcgcaac cgtccggttc    3300
tgaacctgtc ttccctgcgt gcgcagctgt ctcaccgtct ggtgctgaaa caccatcacc    3360
accatcatca ccaccaccat taactcgagt ctaga                              3395
```

<210> SEQ ID NO 2
<211> LENGTH: 1114
<212> TYPE: PRT
<213> ORGANISM: Tomato

<400> SEQUENCE: 2

```
Met Gly Lys Thr Ile Gln Val Phe Gly Phe Pro Tyr Leu Leu Ser Ala
1               5                   10                  15

Glu Val Val Lys Ser Phe Leu Glu Lys Tyr Thr Gly Tyr Gly Thr Val
            20                  25                  30

Cys Ala Leu Glu Val Lys Gln Ser Lys Gly Gly Ser Arg Ala Phe Ala
        35                  40                  45

Lys Val Gln Phe Ala Asp Asn Ile Ser Ala Asp Lys Ile Ile Thr Leu
    50                  55                  60

Ala Asn Asn Arg Leu Tyr Phe Gly Ser Ser Tyr Leu Lys Ala Trp Glu
65                  70                  75                  80

Met Lys Thr Asp Ile Val Gln Leu Arg Ala Tyr Val Asp Gln Met Asp
                85                  90                  95

Gly Ile Thr Leu Asn Phe Gly Cys Gln Ile Ser Asp Asp Lys Phe Ala
            100                 105                 110

Val Leu Gly Ser Thr Glu Val Ser Ile Gln Phe Gly Ile Gly Leu Lys
        115                 120                 125

Lys Phe Phe Phe Leu Ser Ser Gly Ser Ala Asp Tyr Lys Leu Gln
    130                 135                 140

Leu Ser Tyr Glu Asn Ile Trp Gln Val Val Leu His Arg Pro Tyr Gly
145                 150                 155                 160

Gln Asn Ala Gln Phe Leu Leu Ile Gln Leu Phe Gly Ala Pro Arg Ile
                165                 170                 175

Tyr Lys Arg Leu Glu Asn Ser Cys Tyr Ser Phe Lys Glu Thr Pro
            180                 185                 190

Asp Asp Gln Trp Val Arg Thr Thr Asp Phe Pro Pro Ser Trp Ile Gly
        195                 200                 205

Leu Ser Ser Ser Leu Cys Leu Gln Phe Arg Arg Gly Val Arg Leu Pro
    210                 215                 220

Asn Phe Glu Glu Ser Phe Phe His Tyr Ala Glu Arg Glu Asn Asn Ile
225                 230                 235                 240
```

-continued

```
Thr Leu Gln Thr Gly Phe Thr Phe Phe Val Ser Gln Lys Ser Ala Leu
                245                 250                 255
Val Pro Asn Val Gln Pro Pro Glu Gly Ile Ser Ile Pro Tyr Lys Ile
            260                 265                 270
Leu Phe Lys Ile Ser Ser Leu Val Gln His Gly Cys Ile Pro Gly Pro
        275                 280                 285
Ala Leu Asn Val Tyr Phe Phe Arg Leu Val Asp Pro Arg Arg Asn
    290                 295                 300
Val Ala Cys Ile Glu His Ala Leu Glu Lys Leu Tyr Ile Lys Glu
305                 310                 315                 320
Cys Cys Tyr Asp Pro Val Arg Trp Leu Thr Glu Gln Tyr Asp Gly Tyr
                325                 330                 335
Leu Lys Gly Arg Gln Pro Pro Lys Ser Pro Ser Ile Thr Leu Asp Asp
            340                 345                 350
Gly Leu Val Tyr Val Arg Arg Val Leu Val Thr Pro Cys Lys Val Tyr
        355                 360                 365
Phe Cys Gly Pro Glu Val Asn Val Ser Asn Arg Val Leu Arg Asn Tyr
    370                 375                 380
Ser Glu Asp Ile Asp Asn Phe Leu Arg Val Ser Phe Val Asp Glu Glu
385                 390                 395                 400
Trp Glu Lys Leu Tyr Ser Thr Asp Leu Leu Pro Lys Ala Ser Thr Gly
                405                 410                 415
Ser Gly Val Arg Thr Asn Ile Tyr Glu Arg Ile Leu Ser Thr Leu Arg
            420                 425                 430
Lys Gly Phe Val Ile Gly Asp Lys Lys Phe Glu Phe Leu Ala Phe Ser
        435                 440                 445
Ser Ser Gln Leu Arg Asp Asn Ser Val Trp Met Phe Ala Ser Arg Pro
    450                 455                 460
Gly Leu Thr Ala Asn Asp Ile Arg Ala Trp Met Gly Asp Phe Ser Gln
465                 470                 475                 480
Ile Lys Asn Val Ala Lys Tyr Ala Ala Arg Leu Gly Gln Ser Phe Gly
                485                 490                 495
Ser Ser Arg Glu Thr Leu Ser Val Leu Arg His Glu Ile Glu Val Ile
            500                 505                 510
Pro Asp Val Lys Val His Gly Thr Ser Tyr Val Phe Ser Asp Gly Ile
        515                 520                 525
Gly Lys Ile Ser Gly Asp Phe Ala His Arg Val Ala Ser Lys Cys Gly
    530                 535                 540
Leu Gln Tyr Thr Pro Ser Ala Phe Gln Ile Arg Tyr Gly Gly Tyr Lys
545                 550                 555                 560
Gly Val Val Gly Val Asp Pro Asp Ser Ser Met Lys Leu Ser Leu Arg
                565                 570                 575
Lys Ser Met Ser Lys Tyr Glu Ser Asp Asn Ile Lys Leu Asp Val Leu
            580                 585                 590
Gly Trp Ser Lys Tyr Gln Pro Cys Tyr Leu Asn Arg Gln Leu Ile Thr
        595                 600                 605
Leu Leu Ser Thr Leu Gly Val Lys Asp Glu Val Leu Glu Gln Lys Gln
    610                 615                 620
Lys Glu Ala Val Asp Gln Leu Asp Ala Ile Leu His Asp Ser Leu Lys
625                 630                 635                 640
Ala Gln Glu Ala Leu Glu Leu Met Ser Pro Gly Glu Asn Thr Asn Ile
                645                 650                 655
Leu Lys Ala Met Leu Asn Cys Gly Tyr Lys Pro Asp Ala Glu Pro Phe
```

-continued

```
            660                 665                 670
Leu Ser Met Met Leu Gln Thr Phe Arg Ala Ser Lys Leu Leu Asp Leu
        675                 680                 685
Arg Thr Arg Ser Arg Ile Phe Ile Pro Asn Gly Arg Thr Met Met Gly
        690                 695                 700
Cys Leu Asp Glu Ser Arg Thr Leu Glu Tyr Gly Gln Val Phe Val Gln
705                 710                 715                 720
Phe Thr Gly Ala Gly His Gly Glu Phe Ser Asp Leu His Pro Phe
                725                 730                 735
Asn Asn Ser Arg Ser Thr Asn Ser Asn Phe Ile Leu Lys Gly Asn Val
        740                 745                 750
Val Val Ala Lys Asn Pro Cys Leu His Pro Gly Asp Ile Arg Val Leu
        755                 760                 765
Lys Ala Val Asn Val Arg Ala Leu His His Met Val Asp Cys Val Val
        770                 775                 780
Phe Pro Gln Lys Gly Lys Arg Pro His Pro Asn Glu Cys Ser Gly Ser
785                 790                 795                 800
Asp Leu Asp Gly Asp Ile Tyr Phe Val Cys Trp Asp Gln Asp Met Ile
                805                 810                 815
Pro Pro Arg Gln Val Gln Pro Met Glu Tyr Pro Pro Ala Pro Ser Ile
                820                 825                 830
Gln Leu Asp His Asp Val Thr Ile Glu Glu Val Glu Glu Tyr Phe Thr
                835                 840                 845
Asn Tyr Ile Val Asn Asp Ser Leu Gly Ile Ile Ala Asn Ala His Val
        850                 855                 860
Val Phe Ala Asp Arg Glu Pro Asp Met Ala Met Ser Asp Pro Cys Lys
865                 870                 875                 880
Lys Leu Ala Glu Leu Phe Ser Ile Ala Val Asp Phe Pro Lys Thr Gly
                885                 890                 895
Val Pro Ala Glu Ile Pro Ser Gln Leu Arg Pro Lys Glu Tyr Pro Asp
                900                 905                 910
Phe Met Asp Lys Pro Asp Lys Thr Ser Tyr Ile Ser Glu Arg Val Ile
        915                 920                 925
Gly Lys Leu Phe Arg Lys Val Lys Asp Lys Ala Pro Gln Ala Ser Ser
        930                 935                 940
Ile Ala Thr Phe Thr Arg Asp Val Ala Arg Arg Ser Tyr Asp Ala Asp
945                 950                 955                 960
Met Glu Val Asp Gly Phe Glu Asp Tyr Ile Asp Glu Ala Phe Asp Tyr
                965                 970                 975
Lys Thr Glu Tyr Asp Asn Lys Leu Gly Asn Leu Met Asp Tyr Tyr Gly
                980                 985                 990
Ile Lys Thr Glu Ala Glu Ile Leu Ser Gly Gly Ile Met Lys Ala Ser
        995                 1000                1005
Lys Thr Phe Asp Arg Arg Lys Asp Ala Glu Ala Ile Ser Val Ala
        1010                1015                1020
Val Arg Ala Leu Arg Lys Glu Ala Arg Ala Trp Phe Lys Arg Arg
        1025                1030                1035
Asn Asp Ile Asp Asp Met Leu Pro Lys Ala Ser Ala Trp Tyr His
        1040                1045                1050
Val Thr Tyr His Pro Thr Tyr Trp Gly Cys Tyr Asn Gln Gly Leu
        1055                1060                1065
Lys Arg Ala His Phe Ile Ser Phe Pro Trp Cys Val Tyr Asp Gln
        1070                1075                1080
```

```
Leu Ile Gln Ile Lys Lys Asp  Lys Ala Arg Asn Arg  Pro Val Leu
    1085            1090                1095

Asn Leu  Ser Ser Leu Arg Ala  Gln Leu Ser His Arg  Leu Val Leu
    1100             1105                 1110

Lys

<210> SEQ ID NO 3
<211> LENGTH: 21
<212> TYPE: RNA
<213> ORGANISM: Artificial
<220> FEATURE:
<223> OTHER INFORMATION: Primer

<400> SEQUENCE: 3
ggaugcauag cuugaguauu c                                          21

<210> SEQ ID NO 4
<211> LENGTH: 19
<212> TYPE: RNA
<213> ORGANISM: Artificial
<220> FEATURE:
<223> OTHER INFORMATION: Primer

<400> SEQUENCE: 4
cacaggaaac agcuaugac                                             19

<210> SEQ ID NO 5
<211> LENGTH: 21
<212> TYPE: RNA
<213> ORGANISM: Artificial
<220> FEATURE:
<223> OTHER INFORMATION: Primer

<400> SEQUENCE: 5
ggaugcauag cuugaguauu c                                          21

<210> SEQ ID NO 6
<211> LENGTH: 19
<212> TYPE: RNA
<213> ORGANISM: Artificial
<220> FEATURE:
<223> OTHER INFORMATION: Primer

<400> SEQUENCE: 6
cacaggaaac agcuaugac                                             19
```

METHODS AND COMPOSITIONS FOR RNA AMPLIFICATION AND DETECTION USING AN RNA-DEPENDENT RNA-POLYMERASE

CROSS-REFERENCE TO RELATED APPLICATIONS

The present application claims priority to U.S. Provisional Application No. 60/606,222; filed Aug. 31, 2004; entitled METHODS AND COMPOSITIONS FOR RNA AMPLIFICATION AND DETECTION USING AN RNA-DEPENDENT RNA-POLYMERASE which is hereby incorporated herein by reference in it's entirety.

SEQUENCE LISTING

The Sequence Listing submitted on compact disc is hereby incorporated by reference. The two identical compact discs contain the file named 34784_US2.ST25.txt, created on Aug. 31, 2005, and containing 15 kilobytes.

FIELD OF THE INVENTION

The invention relates to methods and compositions used in the amplification of RNA from an RNA template. More specifically, the invention relates to exponentially amplifying an RNA template with an RNA-dependent RNA-polymerase in combination with conditions or agents useful in denaturation or destabilization of a double-stranded RNA molecule.

BACKGROUND OF THE INVENTION

Use of double-stranded RNA as a therapeutic, or to enhance RNAi-based reactions, are topics of interest within the health care and biotechnology industries. However, effective in vitro production of RNA has hindered these interests. In addition, inadequate in vitro production of RNA has limited advancement into other potential fields of RNA use.

Information transfer, and in particular, in vitro synthesis reactions, have traditionally focused on the path of genetic information transfer within a cell that stores information as dsDNA, i.e., from DNA to DNA, from DNA to RNA, and from RNA to protein, i.e., from DNA to RNA to protein. The study of RNA synthesis directly from an RNA template has traditionally received little academic or commercial effort, as few in vivo mechanisms for RNA to RNA transfer have been discovered.

Over the past ten to fifteen years, however, this trend has begun to change with the characterization of RNA viruses and their capacity for in vivo copying of single-stranded RNA to double-stranded RNA. (See, for example, Neufeld et al., 1991, *J. Biol. Chem.* 266(35) 24212-24219). Developments in viral-based genomics, as well as in studies of sequence-specific, RNA-triggered gene silencing, have provided a class of enzymes involved in the potential in vivo synthesis of RNA from RNA template. This class of enzymes, termed RNA-dependent or RNA-directed RNA polymerases (RdRps), are believed to be involved in just such RNA to RNA transfer roles.

It is believed that RdRps had a role in early evolution, when RNA was the primary genetic material of most, if not all, organisms, and used in the synthesis of RNA from RNA. RdRps have been identified in certain RNA viruses, e.g., polio and HIV, as well as in several known eukaryotes. RdRps are involved in genomic replication, mRNA synthesis, RNA recombination, and other like processes. Studies into RdRps have focused on characterization of these enzymes and their potential use in gene silencing studies as well as for targets in drug therapies directed at slowing down or eliminating a RNA viral load from a patient.

Use of RdRps as a tool to replicate an RNA template in vitro has thus far focused solely on non-exponentially forming a double-stranded RNA product from a single-stranded RNA template. RdRps that extend from secondary structure within the templates, as well as non-specifically, have been identified and are in the process of being characterized (U.S. patent Publication No. 2003/0124559 to Makeyev et al). No exponential in vitro amplification reactions have been devised to the inventor's knowledge, especially where oligonucleotide primers are involved. Rather, template ssRNA is replicated in a linear fashion.

Alternatively, it has recently been disclosed that antisense strands of RNA can be synthesized from a sense strand of RNA template, as long as DNA is utilized as an intermediate product of the reaction. This method, termed nucleic acid sequence based amplification (NASBA), calls for the reverse transcription of a sense strand of RNA into an antisense strand of DNA. Reverse transcription is conducted from RNA primed with synthetic oligonucleotides containing T7 RNA polymerase promoter sequence. The original strand of RNA is degraded with RNase H, leaving a single strand of DNA, which is converted back to an antisense strand of RNA using a primer to the DNA strand, and T7 RNA polymerase (Van Gelder et al., *Proc. Natl. Acad. Sci., USA*, 1990, 87(5):1663-1667; HIV QT Nov. 13, 2001). The NASBA method is problematic as RNA must be transcribed to DNA and converted back to RNA using two enzymes, a reverse transcriptase and a T7 polymerase (each having a different fidelity and processivity), as well as the design and preparation of primers having T7 RNA polymerase promoter sequence. These DNA intermediate based RNA amplification reactions also are not exponential in the amplification of product, thereby limiting their effectiveness.

Against this backdrop the present invention has been developed.

SUMMARY OF THE INVENTION

The present invention provides compositions and methods for the in vitro amplification of RNA directly from template RNA. Embodiments of the invention utilize an RNA-dependent RNA-polymerase (RdRp), and preferably a tomato or other cellular RdRp, for the exponential synthesis of target RNA template into de novo synthesized RNA product for diagnostic, therapeutic or other purposes. In contrast to prior art protocols, no DNA intermediate is required for the synthesis of the RNA product. Generally, the RdRp is combined with at least two primers in an amplification reaction mixture and subjected to appropriate amplification reaction conditions, as provided herein.

Accordingly, in one aspect, the invention provides a method for amplifying a target RNA template in vitro, which comprises subjecting the RNA template to an amplification reaction in an amplification reaction mixture comprising an RdRp and at least two primers complementary to target RNA template. The amplification reaction will generally comprise contacting the RNA template with the amplification reaction mixture and incubating said mixture for an appropriate time and under appropriate conditions to produce an RNA product, including at least one denaturation condition such as, e.g., a temperature cycling reaction or alternatively an enzymatic or chemical denaturation reaction.

In a preferred embodiment, the RdRp is a cellular RdRp, and in a particularly preferred embodiment, the RdRp is selected from the group consisting of tomato RdRp, Tobacco RdRp, cucumber RdRp, and wheat RdRp. As explained in more detail herein, the use of viral RdRps is not preferred in view of the error-prone nature of the replication of their genomes and the general lack of fidelity in their RdRps. See, e.g., Pugachev et al., *J. Virol.*, January 2004, 78(2):1032-38; Domingo et al., *The FASEB Journal*, June 1996, 10:859-64; Meyerhans et al., *Origin and evolution of viruses*, 1999, pp. 87-114.

In one embodiment, the denaturation condition is a temperature cycling reaction, typically ranging between 35-90° C. In this embodiment, the amplification reaction mixture is first subjected to an increased temperature range to denature double-stranded RNA template into individual single-stranded RNA, then reduced to a lower second temperature range to facilitate annealing of the primers to the target RNA template and synthesis of the RNA product. The annealing reaction and synthesis reaction may be performed at the same temperature or at different temperatures, as is known in the art, depending on the particular denaturation temperature selected and the thermostability of the selected RdRp, additional RdRp may have to be added after each denaturation reaction.

In another embodiment, the denaturation condition comprises a chemical or enzymatic denaturation reaction. Preferably, the denaturation condition comprises an enzymatic denaturation reaction employing an RNA helicase. Still more preferably, the RNA helicase is selected from the group consisting of EIF4A and eIF4B. Since RNA helicase activity is generally an energy-dependent reaction, in this embodiment the amplification reaction mixture will further comprise the RNA helicase and an energy source such as, e.g. ATP, and optionally a divalent cation such as, e.g. $Mg^{2+}$, $Mn^{2+}$ or $Co^{2+}$.

In another aspect, amplification reaction mixtures are provided comprising a cellular RdRp and at least two primers complementary to a target RNA template. In a preferred embodiment, the reaction mixtures further comprise an RNA helicase, an energy source and optionally a divalent cation such as, e.g. $Mg^{2+}$, $Mn^{2+}$ or $Co^{2+}$. The amplification reaction mixtures may further include RNase inhibitors, RNA stabilizing agents, single-stranded binding proteins, rNTPs and analogs of rNTPs, for the amplification of target RNA into product RNA. An amplification buffer is also provided which is supportive of both RdRp and RNA helicase activity, as described herein.

In another aspect, the invention provides an RNA amplification kit useful for the selective amplification of a target RNA template. The kit comprises an RdRp, preferably a cellular RdRp, and two or more primers complementary to the target RNA sequence in an amplification buffer. In a preferred embodiment, the amplification kit further comprises an RNA helicase, an energy source and optionally a divalent cation such as, e.g. $Mg^{2+}$, $Mn^{2+}$ or $Co^{2+}$. The kit may further comprise a denaturing agent, RNA helicase, RNase inhibitors, RNA stabilizing agents, single-stranded binding proteins, rNTPs and analogs of rNTPs, for the amplification of target RNA into product RNA.

As described in more detail herein, the methods and compositions of the present invention are applicable to sequence-specific amplification. In nature, ssRNA bound to the RISC complex may serve as a primer (Lipardi et. al., *Cell*, 2001, 107(3):297-307; Sijen et al., *Cell*, 2001, 107(4):465-475) for cellular RdRps. In sequence-specific RNA amplification, appropriate primers complementary to the target RNA template sequence are employed along with a suitable RdRp capable of recognizing the primed RNA molecules, as detailed herein. Amplification of the primed RNA template is then allowed to proceed under temperature cycling conditions or in the presence of RNA helicase, under conditions that allow the RNA helicase to unwind the RNA duplex and release all or portions of a ssRNA molecule. Such conditions include, e.g., the presence of ATP and a divalent cation.

In one aspect, the subject compositions and methods find use in siRNA development. In one such embodiment, single-stranded RNA molecules are amplified into dsRNA, in accordance with the present invention, and treated with type III RNase Dicer enzyme (Hannon, *Nature*, Jul. 11, 2002; 418(6894):244-251) to produce dsRNA fragments having 2 nucleotide 3' overhangs useful in transfecting cells for knock-out or knock-down purposes. Dicer-prepared fragments of target dsRNA knock-out/down target mRNA via the host cell's RIS Complex. Such embodiments of the present invention provide significant amounts of target dsRNA for optimizing knock-out/down analysis. Note that three to five different ssRNA molecules per target mRNA are often required in order to find appropriate siRNA with strong silencing effects.

In another aspect, the subject compositions and methods find use in the detection of RNA in a sample, such as, e.g., determining the presence of a target mRNA or viral RNA in a sample. In one embodiment, a sample is contacted with RdRp, RNA helicase and primers specific for a target mRNA or viral RNA sequence, and the target mRNA or viral RNA is amplified thereby providing a much more sensitive test for mRNA presence. For example, detection of a target mRNA in a biopsy sample from a patient can be accomplished using the present invention, providing an early warning sign to the patient that the test cells are at a higher risk of developing into a disease state, or of the actual presence of the disease state. Alternatively, the compositions and methods may be employed as a sensitive detection test for the presence of pathogenic organisms such as, e.g., RNA viruses and the like, using primers specific for a desired target viral RNA sequence.

In another aspect, the subject composition and methods find use in gene expression profiling and analysis without the need of reverse transcription of RNA into cDNA. A true measure of mRNA levels can be determined without the inherent bias of virally derived reverse transcriptases. In one embodiment, a sample is contacted with RdRp, primers specific for a target mRNA sequence, and the target mRNA. The reaction is cycled to generate a comparative expression signal when compared to a housekeeping gene target. For example, gene expression profiles of cancer markers can be compared to housekeeping genes in order to determine the up- or down-regulation of the cancer marker.

In another aspect, methods and compositions for the isothermal amplification of RNA template directly into RNA product is provided, comprising combining the RNA template with an RdRp and an RNA helicase in an amplification reaction mixture and incubating the mixture for a sufficient length of time and under conditions that allow the RNA helicase to unwind the RNA duplex and release all or portions of the ssRNA product. Such conditions include, e.g., the presence of ATP and a divalent cation.

Finally, embodiments of the present invention provide compositions and methods for storing less stable ssRNA molecules as more stable dsRNA molecules. By employing the in vitro amplification compositions and methods of the invention, target ssRNA can be amplified and the reaction stopped to provide dsRNA molecules for storage purposes.

These and various other features as well as advantages which characterize the invention will be apparent from a reading of the following detailed description and a review of the appended claims.

DETAILED DESCRIPTION OF THE INVENTION

Definitions

Figure 1:
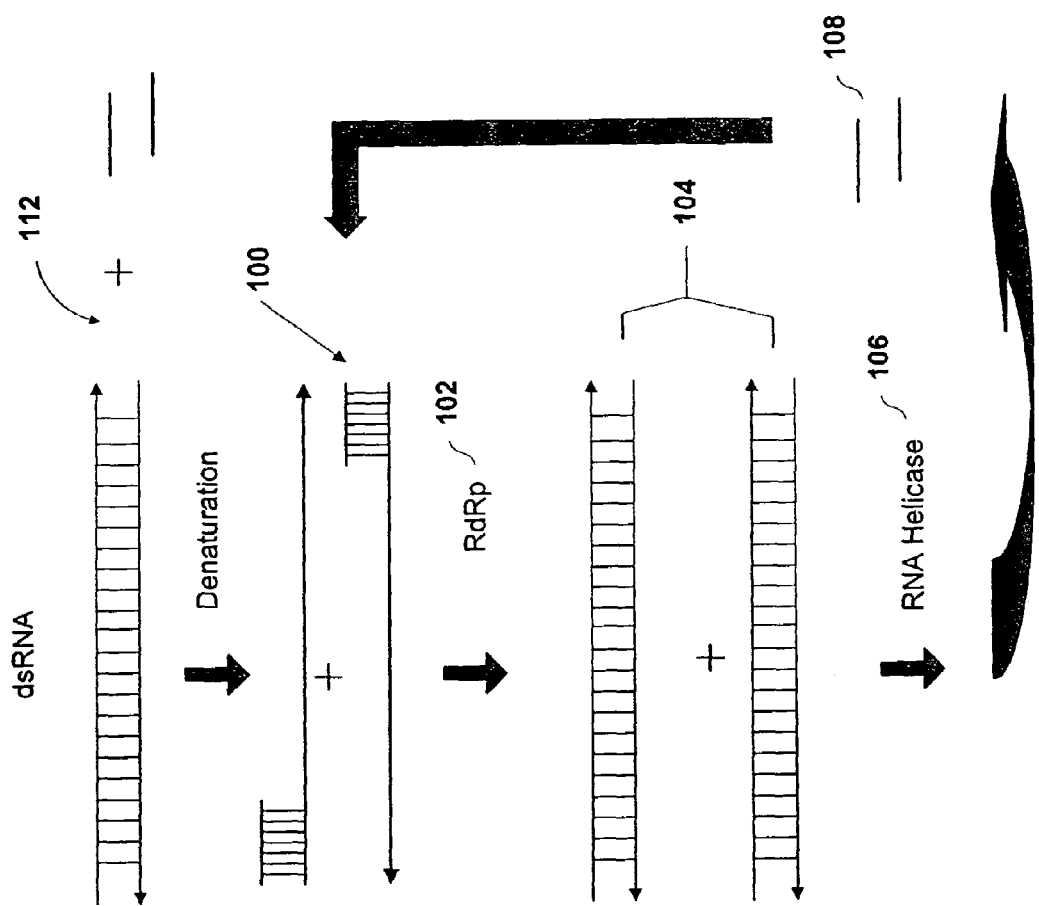
FIG. 1 illustrates a diagram or flow chart for amplifying a double-stranded RNA from an RNA template in accordance with an embodiment of the present invention.

The following definitions are provided to facilitate understanding of certain terms used herein and are not meant to limit the scope of the present disclosure.

"Amplification" refers to repetitive uni- or bi-directional nucleic acid synthesis of a region of nucleic acid.

"Antisense" refers to polynucleotide sequences that are complementary to target "sense" polynucleotide sequences.

"Cellular RdRp" refers to RdRp derived from a cellular, non-viral, source. Cellular RdRp are functional for at least the uses described herein. Illustrative cellular RdRp enzymes are those derived or purified from tomato plants (see Examples below), tobacco plants, or *Neurospora*. Typically, cellular RdRp have a higher fidelity than corresponding RdRp enzymes encoded by viral sources.

"Complementarity" or "complementary" refers to the ability of a nucleotide, or nucleotide analog, in a polynucleotide molecule to form a base pair with another nucleotide, or nucleotide analog, in a second polynucleotide molecule. Complementarity may be partial, in which only some of the nucleotides match according to base pairing, or complete, where all the nucleotides match according to base pairing.

"Denaturing condition" or "denaturing agent" refer to conditions or agents that either enzymatically, chemically or via modification of heat input (temperature) result in the separation of double-stranded RNA into single-stranded RNA. Typically, conditions and agents useful in the present invention minimize RNA strand degradation, and include RNA helicase, temperature cycling between about 35° C. and 90° C. and chemical destabilizing agents, such as polyols.

"Effective amount" refers to an amount sufficient to produce a selected effect. For example, an effective amount of RNA amplification primers is an amount sufficient to amplify a target RNA using the methods of the present invention.

"Homology" refers to the degree of identity between polynucleotides. "Identity" refers to the percentage of identical nucleotides being present at corresponding positions when two nucleic acid sequences are aligned to provide a maximal level of identical nucleotides at the corresponding positions.

"Host cell(s)" refers to cells containing a target nucleic acid molecule, for example heterologous nucleic acid molecule, that are typically suitable for replicating the nucleic acid molecule of interest. Examples of suitable host cells useful in the present invention include, bacterial, yeast, insect and mammalian cells. Specific examples of such cells include, SF9 insect cells, (Summers and Smith, 1987, Texas Agriculture Experiment Station Bulletin, 1555), Chinese Hamster Ovary (CHO) cells (Puck et al., 1958, Proc Natl Acad Sci USA 60:1275-1281), *E. Coli* DH5α cells, as well as various other bacterial cell sources: DH10b cells, XL1Blue cells, XL2Blue cells, Top10 cells, HB101 cells, and DH12S cells.

"Isothermal", "isothermally" or "isothermal conditions" refers to reaction conditions wherein the designated reaction (e.g., amplification) occurs at a single temperature or within a narrow temperature range, typically within about 5-10° C., preferably within about 3-7° C., more preferably within about 0 or 1 or 2 to 5° C., most preferably within about 0 to 2 or 3° C.

"Mesophilic" temperatures are temperatures that do not exceed about 40° C. to about 45° C., and preferably do not exceed about 43° C. Exemplary mesophilic conditions are temperature conditions such that temperature is not a major causative factor in denaturation of dsRNA into ssRNA.

"Nucleic acid sequence" refers to the order or sequence of nucleotides along a strand of nucleic acid. The order of nucleotides typically directs the order of amino acids along a polypeptide chain. A nucleotide sequence can therefore code for the amino acid sequence of a resultant polypeptide.

"Nucleotide analogs," "nucleotide analogues" or "rNTP analogs" refers to sugar or backbone modified ribonucleotides as well as nucleobase modified ribonucleotides that contain a non-naturally occurring nucleobase instead of a naturally occurring nucleobase. Examples include 5-bromo uridine, adenosines and guanosines modified at the eight position, and ribonucleotides as per the technology of Dharmacon, Inc are included also that one or more modified ribonucleotides may be present in any dsRNA of the present invention.

"Primer" refers to one or more oligonucleotides (naturally occurring or synthetic) capable of acting as a point of initiation of synthesis by RdRp along a complementary strand of template ssRNA when placed under conditions in which synthesis of a primer extension product is catalyzed. Primers are preferably single-stranded for maximum efficiency in RNA amplification. Note also that for purposes of the present invention, primer also refers to cases where some ambiguity in the information regarding the terminal sequence(s) of the fragment to be amplified exists. For example, in the case where a RNA sequence is inferred from protein sequence information a collection of primers containing sequences representing all possible condon variations based on degeneracy of the genetic code can be used for each strand. One primer from this collection will be homologous with the end of the desired sequence to be amplified.

"Protein," "peptide," and "polypeptide" for purposes of the present invention are interchangeable and denote a polymer of amino acids or a set of two or more interacting or bound polymers formed from amino acids.

RNA helicase activity refers to functional activity for separating double-stranded RNA to single-stranded RNA. Strand separation of the double-stranded RNA does not have to be complete, but only sufficient to allow primer specific elongation off of the separated RNA strands by RdRp. RNA helicase activity may be a separate activity from the RdRp or may be an inherent characteristic of certain family members of RdRp.

"Isolated" and "purified" for purposes of the present invention are interchangeable, and refers to a polynucleotide or polypeptide that has been separated from cellular debris.

"Wild-type" refers to a nucleic acid molecule or resultant protein expressed from the nucleic acid molecule having characteristics of that same nucleic acid molecule or resultant protein from a native or naturally occurring source.

"Sample" or "source" refers to any substance containing or presumed to contain a target RNA. The sample can come from a cell or cells, a tissue, fluids, or other like material that has been isolated or is itself an organism, e.g., skin, plasma, serum, spinal fluid, blood, tumors, plant, cell culture, viruses etc.

"Synthesize," "synthesized" or "synthetic" refers to the non-exponential, unidirectional filling-in reaction of nucleotides along a template nucleic acid to form a nucleic acid polymer complementary to the template nucleic acid molecule.

"Target RNA" refers to a region of RNA which is to be amplified, detected or both. The target RNA generally resides between the two primer sequences, where appropriate, used for amplification.

Overview

Embodiments of the present invention provide compositions and methods for the exponential amplification of RNA from target RNA sequences. The embodiments of the invention provide a clear advantage over known RNA synthesis techniques by providing a sequence-specific, exponential amplification method that does not require the use of a reverse transcriptase or T7 RNA polymerase.

Embodiments of the present invention incorporate a cellular RNA-dependent RNA-polymerase (RdRp) to amplify RNA. Methods of the invention involve RdRp-directed synthesis of de novo RNA molecules from template RNA employing a denaturation condition (e.g. temperature cycling or RNA helicase activity) to denature the RNA product molecules and provide substrate for additional rounds of RNA amplification. Primers complementary to a target RNA sequence are included for the sequence-specific amplification of product RNA from a desired target RNA. The newly-synthesized ssRNA is then available for additional or cyclical rounds of sequence-specific RNA amplification, with a resultant increase in signal generation.

In some embodiments of the present invention, RdRp synthesizes de novo double-stranded RNA from template single-stranded RNA. The newly synthesized dsRNA product is now available for storage as a more stable dsRNA.

The RNA-dependent RNA-polymerase enzymes employed in the subject compositions and methods can selectively target and amplify specific RNA molecules, and preferably exhibit good fidelity. These RdRp enzymes are preferably derived from cellular sources such as, e.g., a tomato, tobacco or other like plant, and not from viral sources. Notably, cellular RdRps typically have higher fidelity as compared to viral RdRp, an important aspect of the invention, where every error in amplification is magnified by subsequent rounds of amplification. Further discussion regarding RdRp for use with the present invention is provided below.

Embodiments of the present invention also generally provide methods and compositions for the detection of RNA in an RNA-containing sample, including detection of sequence-specific RNA in an RNA-containing sample. For example, methods and compositions of the present invention can be used in the detection of mRNA induced in cells that have been treated with a signaling molecule of interest or treated with environmental modifications. mRNA is detected via amplification of all or selective mRNA molecules dependent on the RdRp and primer combinations utilized. Detection of RNA from pathogenic organisms such as, e.g., RNA viruses, may likewise be accomplished.

Other embodiments of the present invention include using the subject compositions and methods to bolster or enhance an siRNA (or RNAi) reaction by providing an increased amount of dsRNA complementary to at least a portion of a target RNA template. Increased levels of dsRNA can be fragmented by "Dicer" enzyme or other like enzyme for propagating the silencing reaction, as is discussed in greater detail below. Target dsRNA have substantial sequence identity to a portion of the target gene that is targeted for inhibition. Note that RNA sequences with insertions, deletions, and single point mutations relative to the target sequence can also be used for effective inhibition.

As briefly noted above, the majority of the embodiments of the present invention are dependent upon the type of RdRp used in the in vitro RNA synthesis reaction. However, other parameters are also relevant to the invention, for example, the denaturation condition used to denature the duplex RNA into single-stranded RNA, the type of rNTP and whether rNTP analogs can be substituted for standard rNTPs where appropriate for RdRp. It should be noted that certain rNTP analogs can enhance the RNA product stability, provide target glycosylation sites within RNA products, and the like, thereby enhancing the flexibility of the present invention.

Note that embodiments of the invention also include methods of gene therapy, methods for determining the function of a target gene, kits to carry out in vitro RNA amplification and the like.

The practices of the present invention will generally also employ conventional techniques of molecular biology, microbiology, recombinant DNA techniques, biochemistry and the like, which are well within the skill in the art. A number of techniques useful in conjunction with the present invention are described in Sambrook, Fritsch & Maniatis, *Molecular Cloning: A Laboratory Manual*, Second Edition (1989), *A Practical Guide to Molecular Cloning* (Perbal, 1984), and *Nucleic Acid Hybridization* (Hames & Higgins, eds.) (1984).

RNA-Dependent RNA-Polymerases

RNA-dependent RNA-polymerases (RdRps) constitute a family of enzymes that synthesize RNA from RNA template. Most identified RdRps are encoded by a family of RNA viruses where the enzymes are involved in genomic replication, mRNA synthesis and other like processes. Recently, putative RdRps have also been identified outside the viral context, for example in the nematode *Caenorhabditis elegans*, in *Giardia*, and in the fruit fly *Drosophila*. In general, these RdRps have been identified as "cellular" RdRps, i.e., non-virally encoded RdRps, where they are implicated in RNA turnover, possibly as a defense mechanism against invading viruses, i.e., involved in synthesizing ssRNA into dsRNA and degradation of such via the Dicer enzyme. Lipardi et al., *Cell*, 2001, 107(3):297. In addition, several plant species, including tomato and tobacco plants, have been shown to express RdRps, where the enzymes have also been implicated in RNA turnover. Schiebel et al., *Plant Cell*, December 2003, (10), pp. 2087-101. Table 1 illustrates a list of RdRps useful in embodiments of the present invention, along with each enzyme's synthesis targeting mechanism, i.e., what if any priming mechanism is required by the enzyme. Note that native RdRps appear to be missing from archaea and bacteria.

RdRps, like other RNA polymerases, present a structure similar to a right hand, with palm, thumb, and finger domains. The palm domain is the catalytic core for polymerase enzymes, having four sequence motifs preserved throughout all polymerase family members, RNA and DNA. Ahlquist, *Science,* (2002) 296:1270. Palm domains have an RNA-recognition motif, (RRM)-like fold, which has been shown to have low fidelity in most virally derived RdRps (approximately $10^3$-$10^4$). Fidelity in cellular RdRps is better than viral RdRps, having error rates that are predicted to be better than the viral RdRps. See, e.g., Pugachev et al., *J. Virol.,* January 2004, 78(2):1032-38; Domingo et al., *The FASEB Journal,* June 1996, 10:859-64; Meyerhans et al., *Origin and evolution of viruses,* 1999, pp. 87-114.

Cellular RdRps have recently been implicated in RNA silencing mechanisms. Data suggests that RdRps are required for potency and spread of RNA silencing responses. For example, experiments in *Neurospora* and *C. elegans* have illustrated that loss of the RdRp gene prevents RNA silencing. Cogoni et al., *Nature,* 1999, 399:166. In that context, it has been shown that the presence of dsRNA, formed by RdRps, triggers the activation of a sequence-specific RNA degradation system, i.e., dsRNA broken down by the ribonuclease Dicer enzyme into 21-25 nucleotide (nt) fragments called small interfering RNA (siRNA). Iyer et al., *BMC Structural Biology,* January 2003, 3(1):1. The siRNA then propagates the response by interacting with RISC complex (Hammond et al., *Science,* 2001, 293:1146), thereby acting as new primer on ssRNA for RdRp, where additional dsRNA is produced and attacked by the Dicer enzyme and the cycle propagates.

As noted briefly above, RdRps have been characterized that can synthesize new strands of RNA from a primed template, from an unprimed template or from either a primed or unprimed template.

RdRps have been identified that recognize and synthesize RNA from single-stranded RNA templates in the absence of primer. Illustrative of this type of priming mechanism is an RdRp of hepatitis C virus (HCV), termed NS5B. NS5B has been characterized as the RdRp responsible for replicating the HCV RNA genome. Recently, NS5B was cloned, expressed, purified and characterized for its ability to transcribe different RNA substrates. NS5B has been demonstrated to catalyze the elongation of RNA synthesis by either self-priming, extending an existing primer, or initiating RNA synthesis de novo. Luo et al., *J. Virol.,* 2000, 74(2): 851-853. In this manner NS5B is most useful as an enzyme that can synthesize dsRNA from any ssRNA template in the absence of primer, as it will synthesize new RNA strands regardless of priming condition. NS5B, therefore, is integral to non-selectively amplifying a population of RNA, for example, enriching all the RNA within a sample or detecting the presence of any RNA in a sample.

RdRps have also been identified that recognize and synthesize RNA from a primed single-stranded RNA template. Several references detail RdRps that can be used in this context, for example, Schiebel et al., *J. Biol. Chem.,* 1993, 268(16):11858-11867 or Tang et al., *Genes and Dev.,* 2003, 17(1):49-63. In these cases, the RdRp can be used to selectively amplify a target population of RNA.

As noted above, RdRps of the invention are preferably derived from cellular sources. An RdRp derived from a viral source generally has a lower fidelity than a corresponding RdRp derived from a cellular source. As such, cellular-derived RdRps should be used where accurate synthesis of the template RNA is crucial, while viral RdRps can be used where the actual sequence of the RNA is not as important as the fact that RNA is present in a sample, for example, where an assay is performed to determine the mere presence of RNA.

As such, there are a number of relevant parameters for determining a source of RdRp for use in RNA synthesis in accordance with different embodiments of the present invention. Parameters include: the intended use of the RdRp, for example whether specific or non-specific RNA synthesis is required, i.e., does the RdRp recognize and synthesize new target RNA from a primed or un-primed RNA, whether higher fidelity of the enzyme is required for the particular use, i.e., viral or cellular RdRp, and how active or processive is the required RdRp. Preferred embodiments of the present invention include RdRp useful in sequence specific, high fidelity, RNA amplification. As such, preferred embodiments of the present invention include the use of cellular RdRp.

TABLE 1

Illustrative RdRps For Use In Amplification Of Target RNA

| Source | Primer Mechanism | Citations |
|---|---|---|
| Bacteriophage phi 6-phl 14 | non-specific or specific | US Patent Publication No. 20030124559, Jul. 3, 2003 |
| Tomato | Specific, can synthesize on selected ssRNAs without primer | U.S. Pat. No. 6,218,142, US Patent Publication No. 20010023067, Sep. 20, 2001 Schiebel et. al. J. Biol. Chem (1993) 268: 11858 |
| Tobacco | — | Ikegami et al. Proc. Natl. Acad. Sci USA (1978) 75: 2122 |
| Cucumber | — | Khan et al., Proc. Natl. Acad. Sci. USA (1986) 83: 2383 |
| Wheat | | Tang et al., Genes and Dev. (2003) 17: 49; Schiebel et al., Plant Cell (1998) 10: 2087 |
| *Caenorhabditis elegans* | Homologous to tomato RdRp | Schiebel et al., Plant Cell (1998) 10: 2087 |
| *Neurospora* | Homologous to tomato RdRp | Schiebel et al., Plant Cell (1998) 10: 2087 |
| *Arabidopsis* | Homologous to tomato RdRp | Schiebel et al., Plant Cell (1998) 10: 2087 |
| *Drosophila* | — | |
| HCV NS5B | non-specific or specific | Ranjith-Kumar et al., J. Virology (2001) 75: 8615 derived from HCV |

Once a particular RdRp has been determined for a particular use, the RdRp can be obtained from either native or recombinant sources. Native viral RdRps, for example, can be isolated from virally infected host cells. Examples include infection of HeLa cells with honey serotype 1 poliovirus using a viral titer and infection methodology as described in Pfeiffer et al., *Proc. Natl. Acad. Sci.* (2003) 100(12):7289-7294. Cellular RdRps can be obtained from cells that express native RdRp where the cells are grown and the RdRp harvested as per Schiebel et al (1993). For example, isolation of tomato RdRp is performed by infection for induction followed by grinding and processing of leaves and purification of the RdRp from the leaves.

RdRps of the invention can also be expressed and isolated as recombinant protein (see Examples below). Using genetic engineering protocols known in the art, recombinant RdRps can be expressed from expression vectors in target host cells.

For example, tomato RdRp sequence is known and could be cloned and expressed using standard of the art techniques (e.g. as described in U.S. Pat. No. 6,218,142, which is incorporated by reference in its entirety herein). Of particular interest in this regard is expression of RdRps using a baculovirus expression system, where recombinant baculoviruses can be constructed using any number of different techniques, for example using the FastBac system according to the manufacturer's specification (GIBCO BRL). See Luo et al., *J. Virology* (2000) p 851-863. RdRps could also be expressed in conventional *E. coli* cloning/expression systems as well.

RNA Helicase:

RNA helicase enzymes are ATPases that convert double-stranded RNA into single-stranded RNA through unwinding activity. In general, RNA helicases have been implicated in a number of cellular processes including ribosome biogenesis, translation initiation, cell growth, and oogenesis. RNA helicases have been characterized from a number of different organisms, including bacteria and humans. Presently, there are three known and related families of RNA helicase enzymes based on their spatial and sequence conservation of eight amino acid motifs. The RNA helicase families include the DEAD-box family of proteins, the DEAH-box family of proteins and the DExH-box family of proteins. Each family of helicase enzymes has a highly conserved motif specific for that enzyme group. For example, DEAD-box family members have an Asp-Glu-Ala-Asp motif, while DEAH family members have an Asp-Glu-Ala-His motif.

DEAD-box proteins have been identified in *Saccharomyces cerevisiae* as well as in several mammalian cells. DEAD-box proteins generally have ATPase A, ATPase B and SAT motifs, all highly conserved. The ATPase A motif is required for ATP binding, ATPase B motif is required for ATPase activity and the SAT motif is specific for helicase activity. One pair of DEAD-box proteins that have been shown to act in concert as an RNA helicase enzyme is the translation initiation factors eIF4A (eukaryotic Initiation Factor 4A) and eIF4B (eukaryotic Initiation Factor 4B). Presently, it is believed that eIF4A unwinds RNA secondary structures in the 5' untranslated region of mRNA, while presence of eIF4B is required for active RNA helicase enzyme activity. Illustrative RNA helicase enzymes from the DEAD-box family of proteins are shown and characterized in Table 2.

DEAH-box proteins have also been identified in *Saccharomyces cerevisiae*. Generally, DEAH-box proteins are believed to be involved in conformational rearrangements of spliceosomal RNAs. As above for DEAD-box proteins, DEAH-box proteins have RNA-dependent ATPase activity. One pair of DEAH-box proteins, identified as RNA helicase enzymes, are Dhr1p and Dhr2p, both required for ribosome biogenesis. Illustrative RNA helicase enzymes from the DEAH-box family of proteins are also shown in Table 2.

The third class of RNA helicase enzymes, DExH-box, can also be used within the context of the present invention. DExH box proteins have a series of highly conserved motifs, as discussed and shown in Western et al., Development, Apr. 12, 2002; 9(7):1569-1581, and function in an analogous manner to the DEAD and DEAH box proteins. Briefly, DExH-box proteins have a VxDExH motif in the ATP binding and hydrolysis site, and unwind dsRNA in an NTP-dependent fashion, and like the DEAD and DEAH proteins play a role in RNA-related processes. One illustrative member of the family for use in the present invention is the HEN2 protein from *Arabidopsis* (as shown in Table 2).

TABLE 2

Illustrative DEAD-, DExH- and DEAH-box Proteins

| Identification | DEAD/DEAH/DExH | Citation |
|---|---|---|
| eIF4A/eIF4B | DEAD-box | Pause and Sonenberg, EMBO J. (1992) 11: 2643 |
| eIF4A/eIF4H | | Pause and Sonenberg, EMBO J. (1992) 11: 2643 |
| crhC | DEAD-box | Chamot et al. J. Bacterio. (1999) 181: 6 1728-1732 |
| csdA | | Jones et al. J. Biochem. (1996) 93: 76-80 and Jiang et al. J. Bacteriol. (1996) 178: 16 4919-4925 |
| HEN2 | DExH-box | Jankowsky et al., Nature (2000), 403: 407 |
| NPH-II | DexH-box | US Patent Application Pub. No. 20030224375 |
| Prp16p | DEAH | Ortlepp et al., RNA, (1998) 4(8): 1007-1018 |
| Prp22p | DEAH | |

Different RNA helicase enzymes of the invention recognize different RNA based structures as targets for unwinding. For example, RNA Helicase A recognizes and unwinds off of a 3' tail of a double-stranded RNA, but has little unwinding activity where the two-strands of the RNA molecule are flush-ended. Helicase A requires energy in the form of nucleotide triphosphates (ribo or deoxyribose) and catalytically unwinds the dsRNA in the 3' to 5' direction. Lee et al., *J. Biol. Chem.* (1992) 267(7):4398. Conversely, eIF4A recognizes and unwinds blunt-ended dsRNA duplexes with fairly high activity. The eIF4A requires ATP as an energy source and has helicase activity in both the 5'-3' and 3'-5' directions. Rogers et al., *J. Biol. Chem.* (2001) 276(16): 12598.

RNA helicase enzymes of the present invention recognize, interact with, and unwind dsRNA into either partial or complete ssRNA molecules. (Lee et.al., *J. Biol. Chem.*, 1992, 267(7):4398-4407). In some embodiments, single-stranded binding protein (SSB) is included with the RNA helicase to coat and help prevent the displaced strands of the dsRNA from re-annealing and re-forming dsRNA. Typical dsRNA targets are from 2 to 20 kbp in length, and are preferably from 5 to 20 kbp in length. In a typical RNA polymerization chain reaction, conditions are provided for optimal RNA helicase activity and for keeping the unwound RNA molecules from immediately re-hybridizing into dsRNA.

RNA helicase buffer conditions correspond to buffer conditions that can be used in conjunction with RdRp, where preferable concentrations for each buffer constituent are presented. Note also that RNA helicase enzymes typically require ATP or other like energy source and a divalent cation, which preferably may be $Mg^{2+}$, $Mn^{2+}$ or $Co^{2+}$.

Preferably, intermediate products, i.e., product RNA molecules that are being unwound by RNA helicase, present single-stranded primer binding sites for primer annealing prior to the intermediate product re-hybridizing back into the original dsRNA molecule. In such case, the primer is at sufficient concentration and of sufficient length to hybridize to the helicase presented primer binding site prior to the complementary strands of RNA re-forming back into a dsRNA molecule.

RNA helicase enzymes of the invention are active under isothermal and, in a preferred embodiment, mesophilic conditions. For example, preferable enzyme conditions are between 2° C. and 60° C., and preferably between 30° C. and 40° C. RNA helicase enzyme activity is also dependent on buffer conditions, preferably including a buffer solution that conforms to both RdRp and RNA helicase activity.

Note that heat stable RNA analogs can also potentially be used in the synthesis of dsRNA from ssRNA. The dsRNA molecules are more able to resist degradation due to heat and therefore can be heated to temperatures above room temperature. In such embodiments, the RNA helicase can be excluded from the reaction conditions, as heat will provide the energy to break the two strands of RNA apart, thereby providing further templates for the amplification reaction. In these reactions, RdRp can be freshly added to the reaction mix after each cycle of temperature variation or when it has been determined that the enzyme has lost some or all of its activity due to the temperature, especially if the temperature goes above 60° C.

Vectors and Host Cells:

The present invention provides vectors containing the polynucleotide molecules of the invention, as well as host cells transformed with such vectors. Any of the polynucleotide molecules of the invention (see Example 1 below) can be contained in a vector, which generally includes a selectable marker and an origin of replication. The vector further include suitable transcriptional or translational regulatory sequences, such as those derived from microbial or viral molecules. Examples of such regulatory sequences include transcriptional promoters, operators, or enhances, mRNA ribosomal binding sites, and appropriate sequences. A promoter nucleotide sequence is operably linked to a RNA-dependent RNA-polymerase or RNA helicase DNA sequence if the promoter nucleotide sequence directs the transcription of the molecule.

Selection of suitable vectors for the cloning of an RNA-dependent RNA-polymerase or RNA helicase will depend upon the host cell in which the vector will be transformed, and, where applicable, the host cell from which the target polypeptide is to be expressed. Suitable host cells include prokaryotes, yeast, and other like organisms. Specific examples include bacteria of the genera *Escherichia, Bacillus, Salmonella,* as well as members of the genera *Pseudomonas, Streptomyces,* and *Staphylococcus;* yeast from the genera *Sacchoromyces, Pichia,* and *Kluveromyces.*

The RNA-dependent RNA-polymerase and RNA helicase polypeptides (see Example I) of the present invention to be expressed in such host cells may also be fusion proteins that include regions from heterologous proteins. Such regions maybe included to allow for example, enhanced purification, increased secretion, and increased stability. For example, a nucleic acid sequence encoding a signal peptide (secretory leader) may be fused in-frame to a RNA-dependent RNA-polymerase so that it is translated as a fusion protein comprising a signal peptide.

Other genetic engineering methods can be used for the production of a RNA-dependent RNA-polymerase or RNA helicase, these include the expression of the polynucleotide molecules in cell free expression systems, in cellular systems, in host cells, in tissues, and in animal models.

Temperature Based dsRNA Denaturation:

In some embodiments of the present invention, dsRNA is partially or completely denatured into ssRNA molecules through cyclic heating. In preferred RNA amplification reactions, the temperature at which extension is performed is between about 25-45° C., more preferably between about 30-40° C.

In a preferred embodiment, the temperature at which primer annealing is performed is between about 45-65° C., more preferably between about 50-60° C., though the optimum temperature is determined by primer length, base content, degree of primer complementarity to template, and other factors, as is known in the art.

In preferred embodiments, the temperature at which denaturation is performed is between about 60°-80° C., more preferably between 65°-75° C., with temperatures at the lower end of the range being preferred for use in combination with chemical denaturing agents. Preferred amplification methods include polymerase chain reactions (using RdRp) involving from about 1 to about 100 cycles, more preferably from about 30 to about 60 cycles, and peak temperatures of from about 60° to about 90° C.

As noted herein, temperature based denaturation or destabilization can be combined with chemical denaturing agents, for example polyols.

RNA Amplification from an RNA Template

In one aspect, the invention provides methods for amplifying an RNA molecule, comprising subjecting the RNA molecule to an amplification reaction in a composition that includes an RdRp.

RNA amplification is a process by which a template RNA is amplified in whole or in part. Thus, the product of a RNA amplification reaction can be completely or partially complementary to the target RNA template. RNA amplification, in accordance with the present invention, is accomplished by extending a primer in the 5'-3' direction, incorporating nucleotides complementary to the bases of the template at each position in the extension product. The primer may be, for example, a synthetic oligonucleotide that hybridizes to a region of a single-stranded RNA template.

Template RNA for use with the present invention can be utilized from any source thought to contain an RNA of interest. For example, starting template or target RNA may be used if it contains or is thought to contain the target sequence desired for amplification. Thus the process may employ, for example either single stranded or double stranded RNA.

It is not necessary that the target RNA be present initially in a pure form; it may be a minor fraction of a complex mixture and the target RNA may contain more than one desired target RNA sequence which may be the same or different. Therefore, the methods of the present invention may be used for producing large amounts of a target RNA sequence, as well as for amplifying simultaneously multiple target RNA located on the same or different RNA molecules.

RNA may be obtained from any source including cloned RNA, RNA from bacteria, yeast, viruses and higher organisms such as plants or animals. RNA may be extracted from blood or other bodily fluids, or tissue material such as amniotic cells. (See for example, Maniatis et al., *Molecular Cloning: A Laboratory Manua,* New York: Cold Spring Harbor Laboratory, 1982, pp 280-281.

Any specific RNA sequence can be produced by the present methods as long as a sufficient number of bases at both ends of the target RNA are known in sufficient detail so that two oligonucleotide primers can be prepared. Oligonucleotide primers will hybridize to different strands of the desired sequence and at relative positions along the sequence such that an extension product synthesized from one primer, when it is separated from its template, can serve as a template for extension of the other primer into a RNA of defined length.

Oligonucleotide primers for use in the present invention may be prepared using any suitable method, such as, for example the phosphotriester and phosphodiester methods or automated embodiments thereof. In one such automated embodiment diethylophosphoramidites are used as starting materials and may be synthesized as described in Beaucage et al., *Tetrahedron Letters*, 1981, 22:1859-1862, which is incorporated by reference in its entirety herein. One method for synthesizing oligonucleotides on a modified solid support is described in U.S. Pat. No. 4,458,006, which is incorporated by referenced in its entirety herein. It is also possible to use a primer which has been isolated from a biological source, for example, a restriction endonuclease digest.

Preferred primers for use with the present invention have a length of from about 2-100, more preferably about 15-50, and most preferably about 20-30 bases.

As a practical manner, the amount of primer added to an RNA amplification reaction of the present invention will generally be in molar excess over the amount of complementary strand (template) when the sequence to be amplified is contained in a mixture of complicated long-chain nucleic acid molecules. A large molar excess is preferred to improve the efficiency of the process.

Ribonucleoside triphosphates, preferably rATP, rCTP, rGTP and rUTP are also generally added to the amplification reaction mixture in adequate amounts.

In one embodiment of the present invention, RNA template is specifically amplified into RNA product. Target RNA is amplified using a combination of an RdRp for the synthesis of RNA, target specific oligonucleotide primers, and temperature cycling to denature the duplex RNA into single-stranded RNA. Typical cycling conditions cover a temperature range sufficient to adequately denature the duplex RNA, allow for primer hybridization and activity of a RdRp.

In another embodiment of the present invention, RNA template is isothermally amplified into RNA product. Target RNA is amplified using a combination of a RdRp for the synthesis of RNA, and RNA helicase for the unwinding of dsRNA into additional template ssRNA. Typical reaction conditions are isothermal, requiring little or no temperature change(s), and preferably mesophilic. As such, temperature is not required for denaturation of the dsRNA molecules. However, most if not all RNA helicase enzymes of the invention require an energy source—for example ATP, or other like source, as well as a divalent cation.

In more detail, and as shown in FIG. 1, an RNA template is hybridized with an RNA primer at its 3'-end 100, the RdRp recognizes the primed ssRNA and synthesizes a complementary strand of the original ssRNA 102. A dsRNA product is produced 104. Temperature cycling conditions are applied to the de novo synthesized duplex RNA 106. In addition, the newly synthesized RNA strand, now single-stranded, presents a second primer binding site for hybridization with a second primer 108 (at the 3'-end of the new strand). RdRp binds to the original and newly synthesized primed ssRNA to begin the cycle anew by copying two new strands of RNA. The reaction is repetitive and can be continued to exponentially and selectivity produce product RNA (much as PCR is used to exponentially amplify DNA from template DNA).

Figure 2:
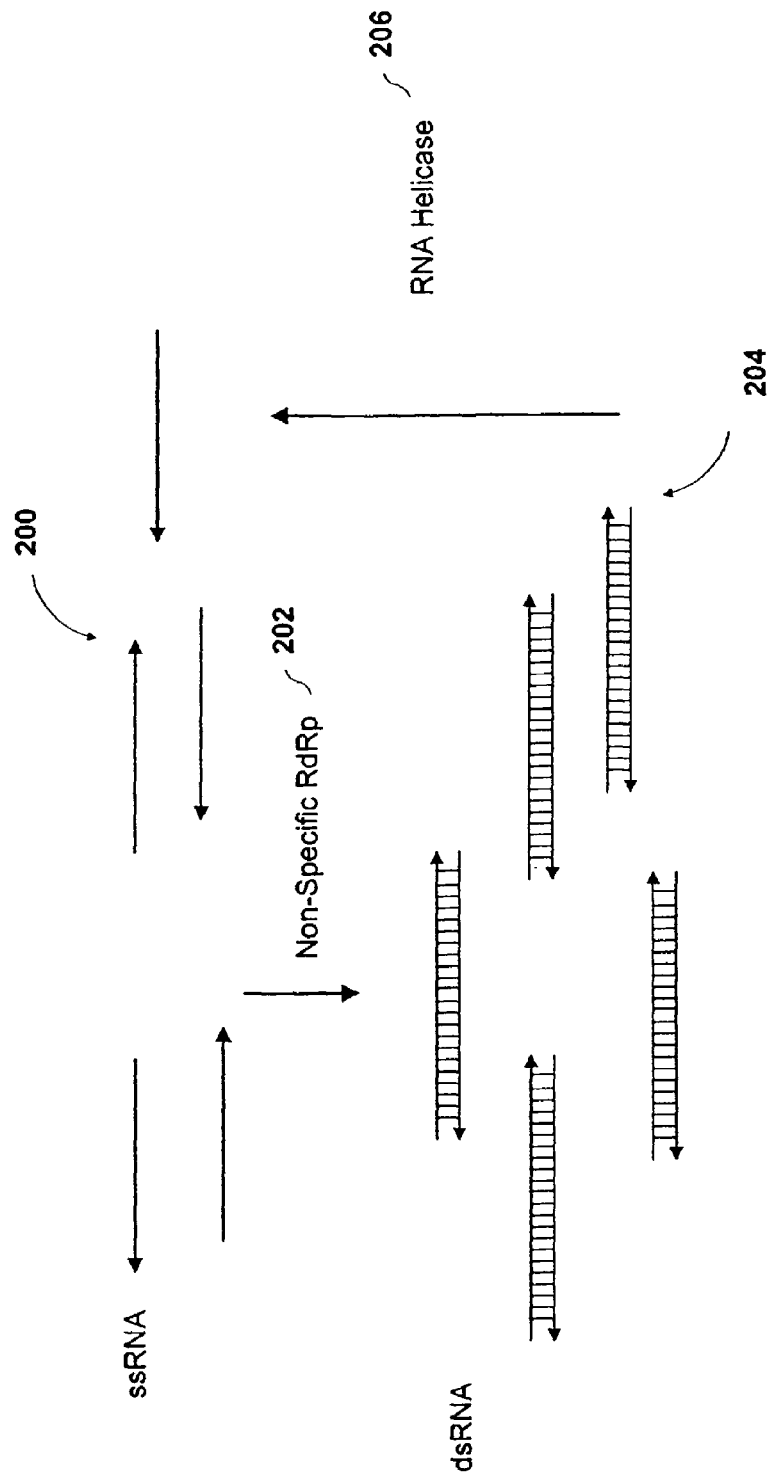
FIG. 2 illustrates a diagram or flow chart for amplifying a double-stranded RNA from an RNA template in accordance with another embodiment of the present invention.

As shown in FIG. 2, an RNA template is hybridized with an RNA primer at its 3'-end 200, the RdRp recognizes the primed ssRNA and synthesizes a complementary strand of the original ssRNA 202. A dsRNA product is produced 204. An RNA helicase recognizes the dsRNA molecule and unwinds the molecule, presenting a first primer binding site for a first primer hybridization 206. In addition, the newly synthesized RNA strand, now single-stranded, presents a second primer binding site for hybridization with a second primer 208 (at the 3'-end of the new strand). RdRp binds to the original and newly synthesized primed ssRNA to begin the cycle anew by copying two new strands of RNA. The reaction is repetitive and can be continued to exponentially and selectively produce product RNA (much as PCR is used to exponentially amplify DNA from template DNA).

In some embodiments of the invention, RdRp and RNA helicase are mixed together in the same reaction mixture with template RNA, RNA primers, rNTPs, and an energy source. In general, an effective amount of each constituent is provided to lead to the amplification of RNA. Alternatively, in some embodiments, the RdRp and RNA helicase can be added to the reaction mixture sequentially to maximize activity, in such case the RdRp is added to the RNA template and the reaction allowed to incubate prior to addition of RNA helicase. In embodiments employing temperature cycling as the denaturation condition, additional enzyme may have to be added with each cycle. In addition, in some embodiments, single stranded binding proteins can be included in the reaction to facilitate the helicase separated strands of RNA from re-annealing prior to binding of either primers or RdRp.

In preferred embodiments of the reaction mixture, carrier protein (BSA), DTT, and RNasin are added to the reaction buffer to optimize RdRp and RNA helicase activity. In one embodiment, the reaction buffer can include: 15-25 mM HEPES-KOH (pH 7.6), 1-3 mM DTT, 25-75 mM KCl (or other like salt), 2-4 mM ATP (or other like energy source dependent on the enzyme), 0.05-0.15 mg/ml bovine serum albumin or other like carrier protein, 1-3 units RNasin or other like RNase inhibitor. In one embodiment, the reaction temperature should remain constant for the duration of the incubation/reaction period, typically from about 30° C. to about 45° C., and preferably from about 35° C. to about 37° C. Note that for certain RdRps the temperature of the reaction may be modified to slightly non-optimal ranges (27° C.-29° C.) in order to slow the polymerase activity down, and thereby potentially increase the fidelity of the enzyme. In another embodiment, the reaction temperature should cycle between 30° C.-90° C., depending on the phase of the reaction (denaturation, hybridization, and de novo synthesis).

RNA helicase activity (e.g., eIF4A or other like enzyme) can be dependent on the presence of helper proteins and associated subunits. These proteins include various initiation factors eIF4B, eIF4H, and the like. Rogers et al., *J. Biol. Chem.*, 2001, 276(16):12598. As an illustrative example, eIF4A concentrations in embodiments of the present invention can be from about 0.1-0.5 μM, and is preferably from about 0.4 μM to about 0.45 μM for about 0.4-0.5 ng of RNA.

In general, RNA helicase concentrations for purposes of embodiments of the present invention are from 0.1-0.5 μM (0-0.1 μg), and preferably from 0.2 μM to about 0.4 μM per 0.4 ng of RNA.

RdRp concentrations for use in embodiments of the present invention include from about 0.5 to about 100 nM, preferably from about 5 to about 30 nM per 100 pm of RNA. RdRp concentration modifications are performed in relation to the activity of the RdRp, the reaction temperature, buffer constituents, and other like parameters.

The target specific primer lengths should be about 2-30 nt and should preferably be from about 15-20 nt. Note also that most viral RdRps will incorporate ribavirin, as well as other rNTP base analogs. Mutation of several viral RdRps can be performed to make a less sensitive enzyme to analogs, which tends to correspond to higher fidelity enzymes. Other mutations can be performed to increase the fidelity of RdRps including changing the active site to fit better RNA and not incorporate incorrect bases.

Table 3 provides a list of different reaction conditions that can be used in the context of amplifying RNA using RdRp and RNA helicase:

TABLE 3

RNA Amplification Buffer Reaction Conditions

| Buffers to Control pH | Divalent Cations as Cofactors | Components For Stabilization | Template/Target Concentration |
|---|---|---|---|
| 0-100 mM Tris-HCl, pH 7.2-8.2 | 0-15 mM $MgCl_2$ | 0-1 mM rNTPs | 50 fmol - 25 nM (0-200 ng) RNA template |
| 0-20 mM Sodium Glutamate, pH 8.2 | 0-15 mM $MgoAC_2$ | 0-0.5% V/V TritonX 100 | Template length - 100-4200 nt |
| 0-20 mM HEPES, pH 7.5 | 0-5 mM $MnCl_2$ | 0-12.5 mM DTT | |
| 0-20 mM HEPES-KOH, pH 7.6 | 0-1 mM $ZnCl_2$ | 0-100 mM KCl | |
| | | 0-1 mM NaCl | |
| | | 0-1 mg/ml BSA | |
| | | 0-30 U RNase Inhibitor (RNasin) | |
| | | 0-20 mM 2-Mercaptoethanol | |
| | | 0-10% glycerol | |

Assays

Among other things, embodiments of the present invention are useful toward amplification of RNA from RNA template. There are a variety of uses for conveniently and exponentially amplifying RNA from RNA template. Embodiments include amplification reactions for specific target RNA. As such, several illustrative assays are described below for integrating RNA amplification from an RNA template.

Enhanced Genetic Inhibition Via Double-Stranded RNA

In one embodiment, the methods and compositions of the present invention are used to knock-out or knock-down, i.e., inhibit a target message(s) in a cell. The method includes amplifying a large pool of target dsRNA and introducing the target dsRNA into a cell so as to inhibit the target gene in that cell. The invention provides methods for producing the large pool of target dsRNA. The methods comprise treating a pool of random ssRNA molecules that includes the target message for inhibition with the compositions of the invention, namely RdRp, RNA helicase (or other denaturing condition or agent) and sequence specific primers. An amplification reaction is then performed on the ssRNA population in accordance with the present invention to prepare a population of target dsRNA molecules. The introduction of dsRNA into the cell can be practiced ex vivo or in vivo.

In more detail, the target gene to be inhibited can be derived from the cell, i.e., cellular/endogenous, can be a transgene, or can be a gene from a pathogen. In addition, the cell itself can be derived from or contained within any organism, e.g., plant, animal, protozoan, bacterium, virus, or fungus. The methods of the present invention can be used to either partially or completely inhibit the target gene within that cell. Inhibition of the target gene can be any detectable decrease in the quantification of gene expression for that gene as compared to a non-treated or negative control of the same gene. Alternatively, functional inhibition of the target gene may also be used to quantitate inhibition of target gene expression; for example, decreased ability of the target gene from mediating the activity of a reporter construct as compared a negative control.

Target dsRNA molecules used in gene inhibition are produced by the RNA amplification methods as described in the present invention. Amplified target dsRNA may be introduced into a cell in an amount, which allows delivery of at least one copy of dsRNA per cell. Benefits of the present invention allow for the delivery of much higher numbers of target dsRNA per cell. Using the methods of the present invention, higher doses of dsRNA are delivered to each cell thereby providing for more effective specific gene inhibition. Note that sequences identical to a portion of the target gene are preferred for inhibition, although sequences having insertions, deletions, mutations and the like may also be effective. Primers are designed to include at least one portion of the target ssRNA that corresponds to the target gene. In alternative embodiments, several portions of the ssRNA can be targeted for amplification and use in the present embodiment. Note that primer design can be optimized using programs known in the art.

Amplified dsRNA can be purified prior to introduction into the cell. For example, amplified dsRNA can be purified using a solvent or resin, precipitation, electrophoresis, chromatography, or a combination thereof. Due to the high yield of dsRNA provided by the amplification methods of the present invention, it is also possible to introduce the dsRNA to the cell in the absence of purification. In either case, the amplified dsRNA can be stored for later use in the inhibition procedure.

Amplified target dsRNA can be introduced into the cell directly, i.e., transfection (for example via lipid- or chemical-mediated transfection), extracellularly, i.e., into a cavity, interstitially, into the circulation of an organism, orally into the organism, and the like.

In principle, once delivered the target dsRNA is acted upon by a "Dicer" enzyme (Tijsterman, M. *Cell*, 2004, 117(1): 1-3) or by RNase III (Yang, D., *Methods of Mol. Biol.*, 2004, 252:471-482) which results in a population of target dsRNA fragments, each having a length of approximately 20-25 nucleotides and having a 1 or 6 nucleotide 3' overhang and more preferably a 1-3 nucleotide 3' overhang. The target dsRNA fragments dissociate into target ssRNA fragments complementary to a portion of the target RNA within the cell. The annealed portions of ssRNA onto target message RNA propagate the silencing effect of inhibiting the target message (using the RIS complex, See Tijsterman, U.S. Pat. No. 6,506,559 B1, and WO 02/44321 A2 as well as U.S. Patent publication No. 2002/0086356 A1, and Zamore et al, *Cell*, 2000, 101:25-33, all of which are incorporated by reference in their entirety). It is also envisioned that the amplified dsRNA not be introduced into the cell, but rather the fragmented dsRNA be introduced into the cell, i.e., the amplified target dsRNA is treated with dicer enzyme prior to introduction into the cell (e.g. according to U.S. Patent publication No. 2005/0059019 to Bulow et al., entitled Gene-related RNAi transfection method). Note also that the amplified dsRNA can be introduced to the cell with other components for enhancing the dsRNA uptake by the cell, promoting annealing of the duplex strands, stabilizing the annealed strands or in some other way contributing to the inhibition of the target gene.

Embodiments of the present invention can be used to introduce dsRNA into a cell for the treatment or prevention of disease, for the modification of a cell's characteristics, i.e., reducing a cells susceptibility to infection by a pathogen, for the study of a gene's function, and other like uses. As an illustrative example, the amplified dsRNA of the present invention can be used to target and treat a known clinical condition, where the amplified dsRNA is injected into the infected cells and the cells machinery propagates the in vivo inhibition of the problematic RNA. Examples include, diseases involving metabolic pathways, where a specific gene product can be decreased or eliminated, resulting in different phenotypes and possible cures of the illness. In such case the dsRNA (fragmented or not) can be introduced in a pharmaceutical composition. Note that using the methods of the present invention, a much greater quantity of dsRNA can be prepared in a much shorter period of time.

Embodiments of the present invention can also be used to assess the ability of amplified dsRNA, and more preferably, amplified fragmented dsRNA, to mediate RNAi. Generally, dsRNA corresponding to a sequence of an mRNA to be degraded is combined with detectably labeled mRNA. Sites of the most effective cleavage are mapped.

RNA Detection

In another embodiment of the present invention, the methods and compositions provide for the detection of the presence of a target RNA in a source, i.e., sample of cells. RdRp, RNA helicase (or other denaturing condition or agent), and oligonucleotide primers specific to the two ends of the sense and anti-sense strand of the target RNA, are mixed with cells believed to express the target RNA. Buffer conditions and energy source are optimized for the RdRp and RNA helicase as previously discussed. The amplification reaction is allowed to proceed to completion. Identification probes or other like detection means are used to determine the presence of the amplified RNA. The methods and compositions of the present invention provide a quick and sensitive method for detection of as little as a few copies of a RNA in a sample, this is a considerable improvement over existing conventional technologies.

Similarly, the methods and compositions of the present invention are used to detect the presence of a target RNA by amplifying total RNA (using a non-specific RdRp, no primers) in a source, and applying the total RNA to a microarray based screen for detection of the target RNA or set of RNA targets. The embodiments of the present invention allow for a more sensitive detection assay of RNA species in a source.

In another embodiment of the present invention, the methods and compositions of RNA amplification are used for real-time RNA amplification and its quantitative detection. For example, real-time RNA amplification can be accomplished in a manner similar to real-time PCR. Amplified RNA can be detected using intercalating dyes in conjunction with real-time thermal cyclers or thermostats with build-in detection units, i.e., no cycling required.

Having generally described the invention, the same will be more readily understood by reference to the following examples, which are provided by way of illustration and are not intended as limiting.

EXAMPLES

Example One

Sub-Cloning, Expression, and Purification of Tomato RNA-dependent RNA-Polymerase 1. Sub-Cloning A nucleic acid sequence for Tomato RNA-dependent RNA-polymerase was codon optimized for expression in *E. coli*, Chemically synthesized and cloned into PJ1 vector by DNA 2.0 (Minlo Park, Calif.). The PJ1 Vector with insert arrived in an agar slab after transformation into XL 1 Blue cells. Colonies from the agar slab were grown overnight at 37° C. in 2YT media (Teknova, Hollister, Calif.). The plasmids were purified using a Prefect Prep Midi kit (Eppendorf AG, Hamburg, Germany) followed by ethanol precipitation. The final pellets were dissolved in 600 μL of molecular biology grade water. The PJ1 vectors were then restriction enzyme digested with NcoI and XhoI (New England Biolabs, Beverly, Mass.) for subcloning into pET19b (Novagen, San Diego, Calif.). The pET19b-RdRP was transformed into BL21 cells and plated onto LB-amp plates (Teknova, Hollister, Calif.) for overnight incubation at 37° C.

Tables 4 and 5 provide the codon optimized tomato RdRp nucleic acid sequence and corresponding tomato RdRp amino acid sequence (SEQ ID NO: 1 and 2 respectively) for use with embodiments of the present invention.

TABLE 4

Optimized Tomato RdRp Nucleic Acid Sequence
(SEQ ID NO. 1):

```
gaattcccatgggtaaaactattcaagtgttcggctttccatacctgctgtctgctgaagttgtcaagagcttcctggagaaatacaccggttacggtacggtt
tgtgctctggaagttaagcaatccaaaggtggctcccgtgctttcgcaaaagtacagttcgctgacaacatctctgcggacaaaatcattaccctggctaac
aaccgtctgtatttcggttcctcctatctgaaagcgtgggaaatgaaaaccgacatcgttcagctgcgtgcttacgtagatcagatggacggcatcaccctg
aactttggctgtcagatcagcgacgacaaattcgcggtactgggttccaccgaagtatctatccagttcggcatcggcctgaaaaagttcttttttcttcctgtc
ctctggtagcgccgattacaaactgcagctgtcttatgaaaacatctggcaggttgtcctgcaccgcccgtatggtcagaacgctcagtttctgctgattcag
ctgttcggtgctcctcgtatttacaaacgtctggaaaactcctgctactccttcttcaaagaaaccccggacgaccagtgggttcgtaccaccgatttcccac
cgtcttggattggcctgagctctagcctgtgcctgcagttccgtcgcggcgtccgcctgccgaactttgaagaatccttcttcactacgcggaacgtgaga
acaacattaccctgcagaccggcttcactttcttcgtttctcagaaatctgcgctggtcccgaacgttcagccgccggagggtatctctatcccgtataaaat
cctgttcaaaatctcctccctggtgcagcacggttgcattccgggtccggcgctgaacgtttacttttttccgtctggttgacccgcgtcgtcgtaatgtcgcct
gtattgagcacgctctggaaaagctgtactacatcaaagaatgctgctacgacccggttcgttggctgaccgagcagtacgatggctacctgaaaggtcg
tcagccgccgaaaagcccaagcatcactctggatgatggcctggtgtacgttcgccgcgttctggttactccttgcaaagttttatttctgtggtccggaagtg
aacgttagcaaccgtgtactgcgcaactattctgaagatatcgataattttctgcgtgtatctttcgttgatgaagaatgggaaaaactgtactctactgacctg
ctgccgaaggcttctactggttccggtgttcgcacgaacatctacgaactgtatcctgtctaccctgcgcaaaggtttcgttattggcgacaaaaagttcgagt
tcctggcgttctcttcttcccagctgcgcgacaacagcgtttggatgtttgcctctcgtccgggtctgactgcgaacgacatccgcgcctggatgggcgact
tcagccagatcaagaatgttgcaaaatacgcggctcgtctgggtcagtccttggctccagccgtgaaactctgtctgtactgcgtcacgaaatcgaagtta
ttcctgacgtcaaagtgcacggtactagctacgtattctctgatggtatcggcaaaatctccggtgacttcgcccaccgcgttgcctccaaatgtggtctgca
gtacactccgtctgcgttccagattcgttacggtggctacaaaggcgtggtaggcgtagatccggactcttctatgaagctgtccctgcgtaaatccatgtct
aagtatgaatccgataacatcaaactggatgttctgggctggtccaagtaccagccgtgctacctgaaccgccagctgatcaccctgctgtccactctggg
tgttaaagacgaggttctggagcagaagcagaaagaagcagttgatcagctggacgctatcctgcacgacagcctgaaggcacaggaagctctggaac
tgatgtcccggtgaaaatactaatattctgaaggccatgctgaactgcggctacaaaccggacgctgaacctttcctgtccatgatgctgcagaccttcc
gtgcgtccaaactgctggacctgcgtacccgtagccgtattttcatcccgaacggtcgcactatgatgggttgtctggatgaatcccgtaccctggaatacg
```

TABLE 4-continued

Optimized Tomato RdRp Nucleic Acid Sequence
(SEQ ID NO. 1):

```
gtcaggtgtttgtgcaattcaccggcgcaggtcatggcgagttttctgatgacctgcacccgtttaataacagccgttctactaactccaacttcatcctgaag
ggtaacgttgtggttgcaaagaacccgtgcctgcacccgggtgacatccgtgtgctgaaagccgtaaatgtacgtgcactgcaccatatggtagattgcgt
ggtattcccgcagaaaggcaagcgtccgcatccaaatgaatgctctggctccgatctggacggtgatatctatttcgtttgctgggaccaggacatgatcc
cgccacgtcaggttcagccgatggaatacccgccggctccatctatccagctggaccacgatgttactatcgaggaagttgaagaatatttcaccaactat
attgtgaacgactctctgggcatcatcgcgaacgcccatgtcgtgttcgcggaccgtgagccggacatggctatgtctgaccgtgcaagaaactggcg
gaactgttttctatcgcagttgactttccgaaaaccggcgtgcctgcggaaatcccaagccagctgcgtccgaaagaatacccggacttcatggataaacc
ggataaaacctcttacatttctgaacgtgttatcggcaaactgttccgtaaagtcaaggacaaagcacctcaagcgagcagcattgcaactttcactcgcga
cgtagctcgtcgttcttatgacgccgatatggaagttgacggtttcgaagattatatcgatgaggcatttgactataaaacggaatatgacaacaaactgggc
aatctgatggactactacggtatcaaaacggaagccgaaatcctgagcggtggtatcatgaaagcctctaagacgttcgatcgtcgtaaggacgctgaag
cgatttctgtggcggttcgtgcgctgcgcaaagaggctcgtgcgtggttcaaacgccgtaacgatattgacgatatgctgccgaaagcctccgcttggtat
cacgttacgtatcaccctacgtactggggctgctataaccaaggtctgaagcgcgctcacttcattagcttcccgtggtgcgtttacgaccagctgatccag
attaagaaagataaagctcgcaaccgtccggttctgaacctgtcttccctgcgtgcgcagctgtctcaccgtctggtgctgaaacaccatcaccaccatcat
caccaccaccattaactcgagtctaga
```

TABLE 5

Tomato RdRp Amino Acid Sequence
(SEQ ID NO. 2):

```
MGKTIQVFGFPYLLSAEVVKSFLEKYTGYGTVCALEVKQSKGGSRAFAKVQFADNISADKIITLANNRLYFG
SSYLKAWEMKTDIVQLRAYVDQMDGITLNFGCQISDDKFAVLGSTEVSIQFGIGLKKFFFFLSSGSADYKLQ
LSYENIWQVVLHRPYGQNAQFLLIQLFGAPRIYKRLENSCYSFFKETPDDQWVRTTDFPPSWIGLSSSLCLQF
RRGVRLPNFEESFFHYAERENNITLQTGFTFFVSQKSALVPNVQPPEGISIPYKILFKISSLVQHGCIPGPALNV
YFFRLVDPRRRNVACIEHALEKLYYIKECCYDPVRWLTEQYDGYLKGRQPPKSPSITLDDGLVYVRRVLVT
PCKVYFCGPEVNVSNRVLRNYSEDIDNFLRVSFVDEEWEKLYSTDLLPKASTGSGVRTNIYERILSTLRKGF
VIGDKKFEFLAFSSSQLRDNSVWMFASRPGLTANDIRAWMGDFSQIKNVAKYAARLGQSFGSSRETLSVLR
HEIEVIPDVKVHGTSYVFSDGIGKISGDFAHRVASKCGLQYTPSAFQIRYGGYKGVVGVDPDSSMXLSLRKS
MSKYESDNIKLDVLGWSKYQPCYLNRQLITLLSTLGVKDEVLEQKQKEAVDQLDAILHDSLKAQEALELMS
PGENTNILKAMLNCGYKPDAEPFLSMMLQTFRASKLLDLRTRSRIFIPNGRTMMGCLDESRTLEYGQVFVQF
TGAGHGEFSDDLHPFNNSRSTNSNFILKGNVVVAKNPCLHPGDIRVLKAVNVRALHHMVDCVVFPQKGKR
PHPNECSGSDLDGDIYFVCWDQDMIPPRQVQPMEYPPAPSIQLDHDVTIEEVEEYFTNYIVNDSLGIIANAHV
VFADREPDMAMSDPCKKLAELFSIAVDFPKTGVPAEIPSQLRPKEYPDFMDKPDKTSYISERVIGKLFRKVK
DKAPQASSIATFTRDVARRSYDADMEVDGFEDYIDEAFDYKTEYDNKLGNLMDYYGIKTEAEILSGGIMKA
SKTFDRRKDAEAISVAVRALRKEARAWFKRRNDIDDMLPKASAWYHVTYHPTYWGCYNQGLKRAHFISFP
WCVYDQLIQIKKDKARNRPVLNLSSLRAQLSHRLVLK
```

2. Expression pET19b-RdRP was transformed into BL21 PlysS (Novagen, San Diego, Calif.) and Rosetta PlysS (Novagen, San Diego, Calif.) and then grown in 2YT media with 100 μg/mL ampicillin at 37° C. until the culture reached 0.8 OD. The cultures were then induced with 1 mM IPTG for 16 hours. After 16 hours, 0.5 mL samples of the cultures were taken and pelleted at 16,000 rpm for 10 minutes. The supernatant was aspirated. 50 μL of Bug Buster (Novagen, San Diego, Calif.) and 2 μL Benzoase (Novagen, San Diego, Calif.) were added to the pellets. The mixture was then vortexed, incubated at room temperature for 20 minutes, and then centrifuged at 16,000 rpm for 10 minutes. Half of the supernatant volume was analyzed by Coomassie staining and half was analyzed by western blot (see FIG. 3).

3. Western Blot Analysis:

The protein gel was transferred onto nitrocellulose using Criterion Blotting Sandwiches (Bio-Rad, Hercules, Calif.). The transfer was run at 35 volts for one hour. After transfer, the nitrocellulose was blocked using 1% dry milk in 1×TBST (Bio-Rad, Hercules, Calif.) and incubated at 4° C. overnight. The blot was then rinsed with 1×TBST and then incubated, with shaking, in a 1:1000 dilution of Mouse Monoclonal Anti-polyhistidine Antibody (Sigma Aldrich, St. Louis, Mo.) for 1 hour at room temperature. The blot was then rinsed three times in 1×TBST. A 1:2000 dilution of Goat-Anti-Mouse IgG(H+L)-AP Conjugate (Bio-Rad, Hercules. Calif.) was added to the blot and incubated, with shaking, at room temperature for 1 hour. After the second antibody, the blot was washed twice with 1×TBST and once with 1×TBS. The blot was developed by adding 1-step NBT/BCIP (Pierce Biotechnology, Rockford, Ill.).

Figure 3:
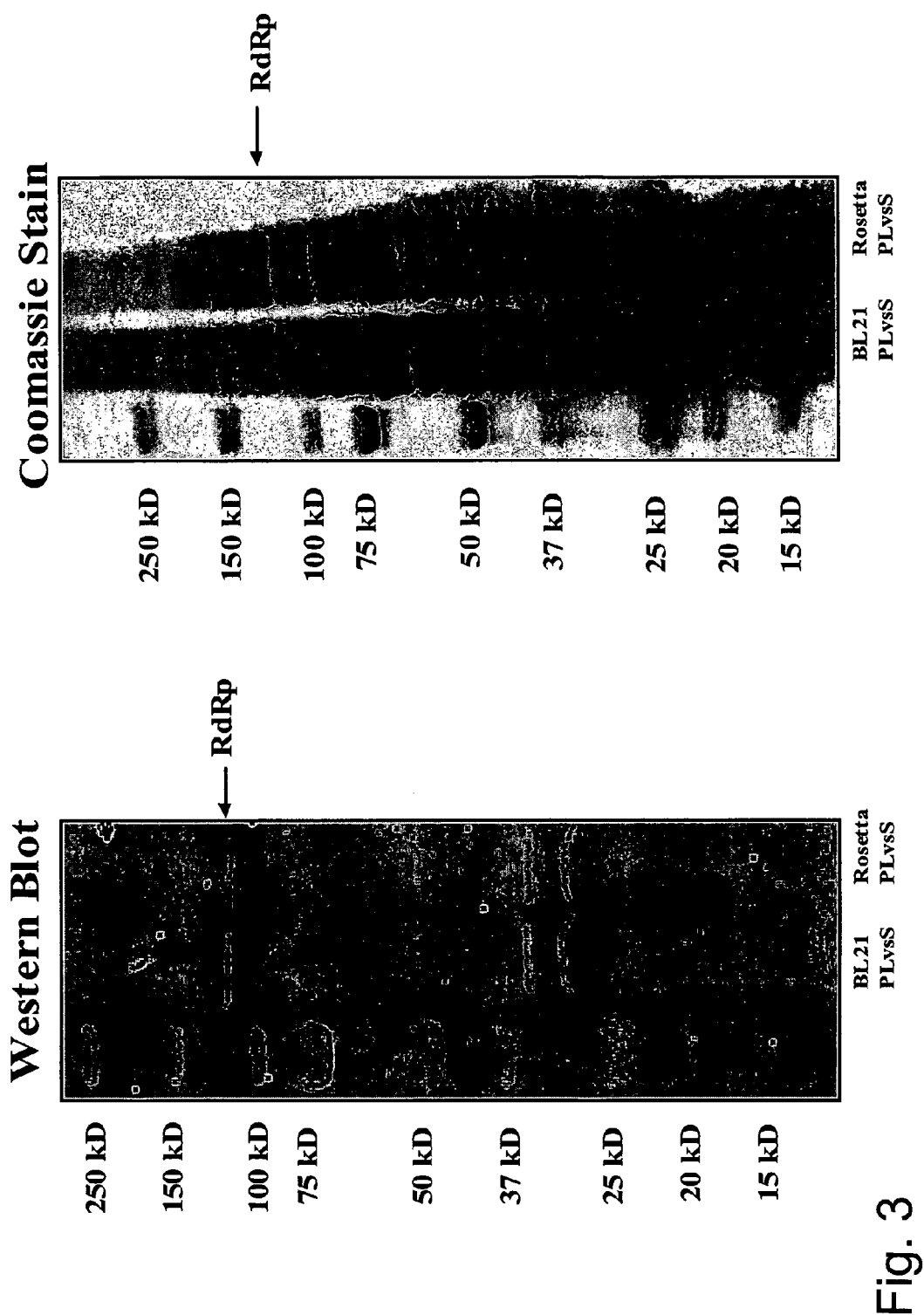
FIG. 3 is a western blot analysis and Coomassie stain analysis of the expression of a tomato derived recombinant RdRp in accordance with embodiments of the present invention.

Results in FIG. 3 show that the tomato RdRp is expressed at high levels within the *E coli* system.

Purification:

After the induction, the cells were spun down at 7000 rpm for 20 minutes in a SLA-3000 rotor. The cells were then stored at −80° C. The cells were resuspended in a lysis solution (20 mM potassium phosphate, 0.5M KCL, 20 mM imidazole, 10 mM BME, 2.5 mM PMSF, pH 7.4) and then homogenized with an Ultra-Turrex 18 homogenizer. The cell lysis solution was then passed three times through a microfluidizer at 18,000 psi. The cell solution was centrifuged at 10,000 rpm in a GSA rotor for 40 minutes, and the supernatant (soluble protein) was filtered and applied to a HisTrap HP 2 mL nickel column (Amershamn Biosciences, Piscataway, N.J.). The protein was eluted off the column with a 20 mM potassium phosphate, 0.5M KC, and 0.5M imidazole elution buffer. Various fractions were analyzed on 4-20% Criterion Tris-glycine denaturing gels (Bio-Rad, Hercules, Calif.) (see FIG. 4).

Figure 4:
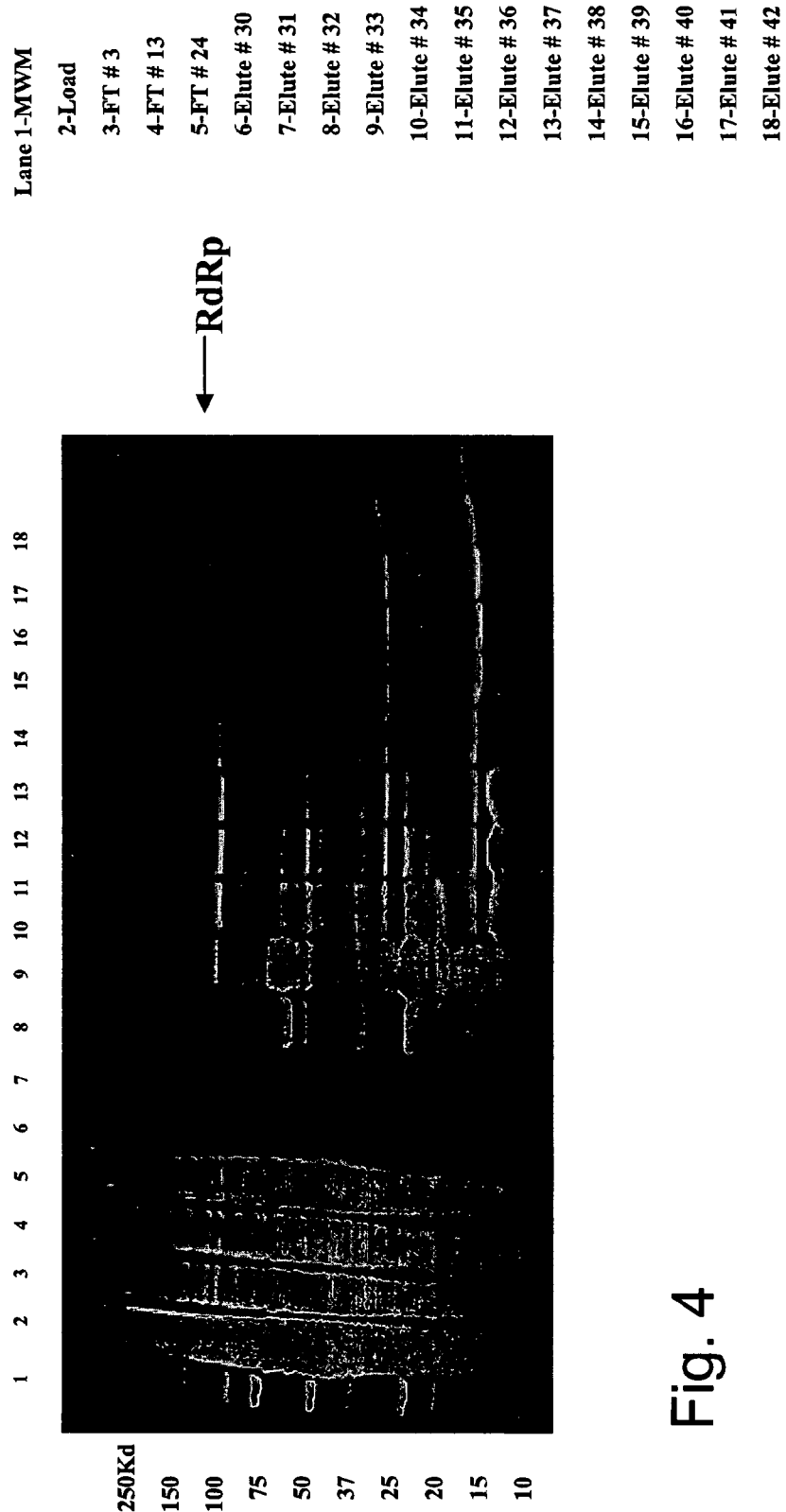
FIG. 4 is a Coomassie stain analysis of the purification of a tomato derived recombinant RdRp in accordance with embodiments fo the present invention.

FIG. 4 illustrates that expressed tomato RdRp can be isolated and purified for use in embodiments of the present invention. Note the high degree of purification attained using the expression and purification scheme of the present invention.

Example Two

Amplification of RNA Template Using Temperature Cycling

The following example is provided to illustrate the prospective utility for amplifying a target RNA, under temperature cycling conditions, using a recombinant tomato RdRP. A reaction mixture having 0.5 µg RdRp, 0.02 pmol target RNA, 100-300 nM primer 1 (SEQ. ID. No. 3) (5'-ggaugcauagcuugaguauuc-3'), 100-300 nM primer 2 (SEQ. ID. No. 4) (5'-cacaggaaacagcuaugac-3'), 0.2-0.5 mM rNTPs in 20 mM Tris-HCL, pH 7.5, 70 mM KCl, 2-10 mM MgoAc, 1.5 mM DTT, 20 U Rnasin or other like RNase inhibitor. A final reaction volume of 20 µL is obtained. The reaction is incubate between 70-85° C. to separate the duplex strands of the template followed by reaction cooling to 35-45° C. During the temperature reduction, the primers bind to the complement sequences on opposite strands of the target RNA. Once the temperature reaches the optimized range, 0.5 µg of RdRp is added to the reaction mixture for strand extension. This process is repeated as many times as desired. Reaction products are analyzed through a combination of spectroscopy and gel electrophoresis.

Expected results would include the formation of duplex RNA amplicon. The intensity of the amplicon band will increase with each additional round of temperature cycling.

Example Three

Amplification of RNA Template Using a RNA Helicase

The following Example is provided to illustrate the prospective utility for amplifying a target RNA using a tomato derived RdRp and an RNA helicase (eIF-4A and eIF-4B) in a single reaction mix. A reaction mixture having 0.5 µg RdRp, 2 µg recombinant eIF-4A, 0.5 µg recombinant eIF-4B, 0.02 pmol target RNA, 100-300 nM primer 1 (SEQ. ID. No. 5) (5'-ggaugcauagcuugaguauuc-3'), 100-300 nM primer 2 (SEQ. ID. No. 6) (5'-cacaggaaacagcuaugac-3'), 0.2-0.5 mM rNTPs in 20 mM Tris-HCl, pH 7.5, 70 mM KCl, 0.5 mM MgoAc, 1.5 mM DTT, 0.5 mM ATP, 20 U RNasin or other like RNase inhibitor is prepared. A final reaction volume of 20 µl is obtained. The reaction is allowed to incubate for approximately 30 minutes to one hour at 35-45° C.

Reaction products are analyzed through a combination of spectroscopy and gel electrophoresis. Note that recombinant eIF-4A and -4B can be obtained using the methods described in Pause et al., *Mol. Cell. Biol.*, 1993, 6789-6798.

Expected results would include the formation of duplex RNA amplicon. The intensity of the amplicon band will increase with incubation time.

Example Four

Amplification of mRNA as Method of Viable Bacteria Detection

Methods currently available for viable bacteria detection require a large number of bacteria be present in order to have enough signal strength for detection, especially as compared to background signal. There are systems, such as PCR, which can amplify very small amounts of DNA present in a sample, however, PCR only indicates that a bacteria contamination is present, not if the bacteria are viable. Protein methods, such as ELISA, can also be used for viable bacteria detection, but sensitivity of protein detection is typically fairly low, thereby limiting the usefulness of this reaction. The transitive nature of RNA makes it a better candidate for detection of viable bacteria, as RNA is rarely present in a non-viable cells, especially cells that have been dead for any length of time.

Using the methods and compositions of the present invention, target RNA of a bacterial contaminate can be amplified. Target RNA, and therefore primers, should be unique to the bacteria or strain of bacteria being tested. Food, water and certain clinical diagnostic applications are analyzed for viable bacteria contamination, where amplification and detection of target RNA indicates presence of viable bacteria. The same technique can be used to detect virulent or lytic infections. In each case, buffers and reactants as described in Example 1 are mixed with samples potentially having viable bacteria, and reaction products viewed on stained agarose gels or via spectroscopy.

It will be clear that the invention is well adapted to attain the ends and advantages mentioned as well as those inherent therein. While a presently preferred embodiment has been described for purposes of this disclosure, various changes and modifications may be made which will readily suggest themselves to those skilled in the art and which are encompassed in the spirit of the invention disclosed herein and as defined in the appended claims.

All patents and publications cited herein are hereby incorporated by reference in their entirety.

---

What is claimed is:

1. An amplification reaction mixture for selectively amplifying RNA from a target RNA template comprising: a cellular RNA-dependent RNA-polymerase and at least two primers complementary to said target RNA template; wherein the RNA-dependent RNA-polymerase is encoded by a nucleic acid sequence comprising SEQ ID NO:1.

2. The reaction mixture of claim 1, wherein said primers are RNA primers.

3. The reaction mixture of claim 1, wherein the cellular RNA-dependent RNA-polymerase is a recombinant cellular RNA-dependent RNA-polymerase.

4. The reaction mixture of claim 1 further comprising an RNA helicase.

5. The reaction mixture of claim 4, wherein the RNA helicase is eIF4A.

6. The reaction mixture of claim 4, further comprising an RNA helicase accessory protein.

7. An RNA amplification kit for selectively amplifying RNA from a target RNA template comprising: a cellular RNA-dependent RNA-polymerase and at least two primers complementary to said target RNA template; wherein the RNA-dependent RNA-polymerase is encoded by a nucleic acid sequence comprising SEQ ID NO:1.

8. The kit of claim 7 further comprising an RNA helicase.

9. The kit of claim 8 further comprising an RNA helicase accessory protein.

10. A method for selectively amplifying RNA from an RNA template, comprising:
   contacting the template RNA with an amplification reaction mixture according to claim 1; and
   incubating said amplification reaction mixture to produce amplified RNA product,
   wherein said incubation step comprises at least one denaturation condition.

11. The method of claim 10 wherein the RNA-dependent RNA-polymerase utilizes oligonucleotide primer-dependent transcription initiation.

12. The method of claim 10 wherein the RNA-dependent RNA-polymerase is a recombinant RNA-dependent RNA-polymerase.

13. The method of claim 10 wherein the primer is composed of RNA.

14. The method of claim 10 wherein the denaturation condition comprises a temperature cycling reaction.

15. The method of claim 10, wherein the denaturation condition comprises an enzymatic denaturation reaction.

16. The method of claim 15, wherein the amplification reaction mixture further comprises an RNA helicase.

\* \* \* \* \*